US008586309B2

(12) United States Patent
Kopan et al.

(10) Patent No.: US 8,586,309 B2
(45) Date of Patent: Nov. 19, 2013

(54) METHODS OF DETERMINING COPY NUMBER OF A GENETIC LOCUS

(75) Inventors: Raphael Kopan, St. Louis, MO (US); Zhenyi Liu, St. Louis, MO (US)

(73) Assignee: Washington University, Saint Louis, MO (US)

( * ) Notice: Subject to any disclaimer, the term of this patent is extended or adjusted under 35 U.S.C. 154(b) by 216 days.

(21) Appl. No.: 13/127,006

(22) PCT Filed: Oct. 30, 2009

(86) PCT No.: PCT/US2009/062804
§ 371 (c)(1),
(2), (4) Date: Jun. 22, 2011

(87) PCT Pub. No.: WO2010/051464
PCT Pub. Date: May 6, 2010

(65) Prior Publication Data
US 2011/0244449 A1 Oct. 6, 2011

Related U.S. Application Data

(60) Provisional application No. 61/110,073, filed on Oct. 31, 2008.

(51) Int. Cl.
C12Q 1/68 (2006.01)
C12N 15/11 (2006.01)
C12N 15/12 (2006.01)
(52) U.S. Cl.
USPC .......................................... 435/6.11; 536/23.1
(58) Field of Classification Search
None
See application file for complete search history.

(56) References Cited

U.S. PATENT DOCUMENTS

| 6,821,734 B2 | 11/2004 | Kambara et al. |
| 2006/0134674 A1* | 6/2006 | Huang et al. ...................... 435/6 |
| 2008/0096766 A1 | 4/2008 | Lee |

FOREIGN PATENT DOCUMENTS

EP 1 229 128 A1 * 8/2002

OTHER PUBLICATIONS

Armour et al., "Accurate, high-throughput typing of copy number variation using paralogue ratios from dispersed repeats" Nucl. Acids Res. 35: 1-8, 2007.
Aten et al., "Methods to detect CNVs in the human genome" Cytogenet. Genome Res. 123:313-321, 2008.
Carter, N. P., "Methods and strategies for analyzing copy number variation using DNA microarrays ," Nat. Genet. 39: S16-S21, 2007.
Charbonnier et al. "Detection of Exon Deletions and Duplications of the Mismatch Repair Genes in Hereditary Nonpolyposis Colorectal Cancer Families Using Multiplex Polymerase Chain Reaction of Short Fluorescent Fragments" Cancer Res. 60:2760-2763, 2000.
Fakhrai-Rad et al., "Pyrosequencing: An Accurate Detection Platform for Single Nucleotide Polymorphisms" Human Mutation 19: 479-485, 2002.
Fanciulli et al., "FCGR3B copy number variation is associated with susceptibility to systemic, but not organ-specific, autoimmunity" Nature Genetics 39: 721-23, 2007.
Guo, D.C., et al., "Universal primer applications for pyrosequencing" Methods Mol. Biol. 373: 57-62, 2007.
Hall et al., The use of pyrosequencing to identify copy number variation of 16p11.2 in euchromatic variant carriers and the normal population. National Genetics Reference Laboratory (Wessex). 2008 [online]. Retrieved from the internet: <URL: http://ngrl.co.uk.Wessex/downloads/pdf/16p_BSHG06.pdf>.
Liu et al., Rapid Identification of homologous recombinants and determination of gene copy number with reference/query pyrosequencing (RQPS). Genome Res., 2009 (Epub Oct. 1, 2009). 19:2081-208.
Murtaugh, L.C., et al. "Notch signaling controls multiple steps of pancreatic differentiation" Proc. Nat'l. Acad. Sci. USA 100: 14920-14925, 2003.
Pielberg et al., A Sensitive Method for Detecting Variation in Copy Numbers of Duplicated Genes. Genome Res., 2003, vol. 13, No. 9, pp. 2171-2177.
Pourmand, N., "Multiplex Pyrosequencing" Nucleic Acids Res. 30, e31, 2002.
Ronaghi et al., "DNA Sequencing: A Sequencing Method Based on Real-Time Pyrophosphate" Science 281: 361-365, 1998.
Ronaghi, M., et al., "Analyses of secondary structures in DNA by pyrosequencing" Anal. Biochem. 267: 65-71, 1999.
Royo, J.L., et al., "Pyrosequencing protocol using a universal biotinylated primer for mutation detection and SNP genotyping" Nature Protocol 2: 1734-1739, 2007.
Schouten et al., "Relative quantification of 40 nucleic acid sequences by multiplex ligation-dependent probe amplification" Nucl. Acids Res. vol. 30, No. 12: 1-13, 2002.
Seo et al., An accurate method for quantifying and analyzing copy number variation in porcine KIT by an oligonucleotide ligation assay. BMC Genetics, 2007, 8:81.
Sequenom QuickGuide: CNV Analysis Using MassARRAY, Absolute Copy Number (ACN). Jun. 12, 2008 [online]. Retrieved from the internet: <URL: http://www.sequenom.com/docs/Absolute%20Number_QuickGuide.pdf>.
Söderbäck et al. "Determination of CYP2D6 gene copy number by pyrosequencing" Clinical Chemistry 51: 522-531, 2005.

(Continued)

*Primary Examiner* — James Martinell
(74) *Attorney, Agent, or Firm* — Saul L. Zackson; Zackson Law LLC

(57) ABSTRACT

Disclosed are methods of determining in a sample, the molar ratio of a query locus to a reference locus, comprising: 1) forming one or more mixtures, each mixture comprising: a) a reference-query coupled probe comprising a nucleobase polymer comprising i) a probe reference locus comprising a probe reference allele, and ii) a probe query locus comprising a probe query allele, and b) a sample comprising i) a sample reference locus comprising a sample reference allele and ii) 0 or greater copies of a sample query locus comprising a sample query allele; 2) for each mixture, determining a) the amount of probe reference allele as a fraction of total reference allele and b) the amount of probe query allele as a fraction of total query allele; and 3) calculating the molar ratio of the sample query allele to the sample reference allele.

18 Claims, 10 Drawing Sheets

(56) References Cited

OTHER PUBLICATIONS

Vooijs, M., et al., "Mapping the consequence of Notch1 proteolysis in vivo with NIP-CRE" Development 134: 535-544, 2007.

Wasson et al., "Assessing Allele Frequencies of Single Nucleotide Polymorphisms in DNA Pools by Pyrosequencing Technology" BioTechniques 32:1144-1152, 2002.

Witt et al., Notch2 Haploinsufficiency Results in Diminished B1 B Cells and a Severe Reduction in Marginal Zone B Cells. J. Immunol., 2003, vol. 171, No. 6, pp. 2783-2788.

Georges et al., "Distinct Expression and Function of Alternatively Spliced Tbx5 Isoforms in Cell Growth and Differentiation" Molecular and Cellular Biology 28: 4052-4067, 2008.

* cited by examiner

METHODS OF DETERMINING COPY NUMBER OF A GENETIC LOCUS

CROSS-REFERENCE TO RELATED APPLICATIONS

This application claims priority from PCT Application No. PCT/US2009/062804 filed Oct. 30, 2009 and U.S. Provisional Application Ser. No. 61/110,073 filed Oct. 31, 2008, each of which is incorporated herein by reference in its entirety.

STATEMENT REGARDING FEDERALLY SPONSORED RESEARCH OR DEVELOPMENT

This invention was made with Government support under grant ROI. DK066408 awarded by the National Institutes of Health. The Government has certain rights in the invention.

INCORPORATION-BY-REFERENCE OF MATERIAL SUBMITTED IN COMPUTER READABLE FORM

The Sequence Listing, which is a part of the present disclosure, includes a computer readable form and a written form. Sequences disclosed in the Sequence Listing in computer readable form are identical to sequences disclosed in the Sequence Listing in written form. The subject matter of the Sequence Listing is incorporated herein by reference in its entirety.

Introduction

There are a wide variety of situations in which a researcher, a clinician or other investigator needs to determine the copy number of a genetic locus in a sample. However, commonly used methods for such determinations, such as Southern blotting, can be slow, inconvenient, inaccurate, and/or lack sensitivity.

Chromosome engineering by random integration (to create transgenic animals) or by homologous recombination (to manipulate specific genes) has been widely used to decipher gene functions and demonstrate disease causality. These techniques however have limitations: the random integration of a transgene into a genome often makes it difficult to distinguish homozygotes from heterozygotes; in gene targeting models, traditional methods for identification of correctly targeted cells (such as embryonic stem cells or iPS), including PCR and Southern blot, limit the size of the homologous arms. Methods recently developed to overcome such limitations (quantitative PCR and FISH screening methods; Valenzuela, D. M., et al., Nature Biotechnol. 21: 652-659, 2003; Yang, Y., and Seed, B. Nature Biotechnol. 21: 447-451, 2003) remain technically challenging. Söderbäck et al. (Clinical Chemistry 51: 522-531, 2005) used pyrosequencing to identify copy number of the CYP2D6*5 and CYP2D6*2xN alleles by coamplifying and sequencing the CYP2D6 gene and the equivalent region in the CYP2D8P pseudogene. However, their methods depended upon the presence of the CYP2D8P (naturally occurring) pseudogene.

SUMMARY

The present inventors have developed methods of determining copy number of a genetic locus in a biological sample. The methods entail determining the molar ratio of a query locus to a reference locus in a sample. In various embodiments, the methods comprise forming at least one mixture comprising: a) a reference-query coupled probe comprising a nucleobase polymer comprising i) a probe reference locus comprising a probe reference allele, and ii) a probe query locus comprising a probe query allele, and b) a sample comprising i) a sample reference locus comprising a sample reference allele and ii) a sample query locus, comprising 0 or greater copies of a sample query allele. In various configurations, a sample query locus can be present in an unknown number of copies, such as 0 copies, 1 copy, 2 copies, or greater. In various configurations, a sample reference locus can comprise one or more copies, and the number of copies can be a known number of copies. In various configurations, the methods further comprise determining, for the mixture, a) the amount of probe reference allele as a fraction of total reference allele (m), or the molar ratio of the probe reference allele to the sample reference allele ($m/(1-m)$), and b) the amount of probe query allele as a fraction of total query allele (n), or the molar ratio of the probe query allele to the sample query allele ($n/(1-n)$). In some configurations, the methods can further comprise calculating the molar ratio of the sample query allele to the sample reference allele. In various configurations, the ratio can be rounded to a positive integer, or a ratio of small integers (such as ½, ⅓, ¼, etc.) A ratio so determined can equal the molar ratio of the reference locus to the query locus in the sample. In some aspects, copy number of the sample query locus can be determined if the copy number of the sample reference locus is known. For example, if the molar ratio of the probe reference allele to the sample reference allele is determined to be 3.7:1 (i.e., $m/(1-m)=3.7$), and the molar ratio of the probe query allele to the sample query allele is determined to be 7.4:1 (i.e., $n/(1-n)=7.4$), then the molar ratio of the sample query allele to the sample reference allele is 1:2. If the sample is, for example, a whole genome sample, the sample reference locus is known to be a diploid locus (i.e., present in 2 copies/genome) and the molar ratio of the sample query allele to the sample reference allele is 1:2, then it can be concluded that the sample query locus is a haploid locus (i.e., present in 1 copy/genome).

In various alternative embodiments, the methods comprise forming a first mixture and at least one second mixture, each mixture comprising: a) a reference-query coupled probe comprising a nucleobase polymer comprising i) a probe reference locus comprising a probe reference allele, and ii) a probe query locus comprising a probe query allele, and b) a sample comprising i) a sample reference locus comprising a sample reference allele and ii) a sample query locus, comprising 0 or greater copies of a sample query allele, wherein the reference-query coupled probe and the sample reference locus have a first concentration ratio in the first mixture, and the reference-query coupled probe and the sample reference locus have at least one second concentration ratio in the at least one second mixture. In various configurations, a sample query locus can be present in an unknown number of copies, such as 0 copies, 1 copy, 2 copies, or greater. In various configurations, the methods further comprise determining, for each mixture, a) the amount of probe reference allele as a fraction of total reference allele (m) or the molar ratio of the probe reference allele to the sample reference allele ($m/(1-m)$), and b) the amount of probe query allele as a fraction of total query allele (n) or the molar ratio of the probe query allele to the sample query allele ($n/(1-n)$). In some configurations, the methods can further comprise calculating the molar ratio of the sample query locus to the sample reference locus. In various aspects, calculating the molar ratio can comprise determining the difference in value of $m/(1-m)$ of two or more mixtures and the difference in value of $n/(1-n)$ of the two or more mixtures. In some configurations, the methods further comprise plotting data points of ($m/(1-m)$) against ($n/(1-n)$) for each mixture, and fitting a line to the data points. The slope of the line (which can be rounded to a whole number or a ratio of small integers such as ½, ⅓ or ¼) can equal the molar ratio of the query locus to the reference locus in the sample. In some aspects, copy number of the sample query locus can be determined if the copy number of the sample reference is known. For example, if the reference locus is known to be a diploid locus, the copy number of the sample query locus is then equal to twice the slope of the line.

In some aspects, a sample reference allele can comprise a sample reference SNP allele, a sample query allele can comprise a sample query SNP allele, a probe reference allele can comprise a probe reference SNP allele, and a probe query allele can comprise a probe query SNP allele. In some configurations, one or both SNP alleles comprised by the reference-query probe can each be an artificial SNP allele.

In some aspects of the present teachings, the molar ratio in a mixture of a probe reference locus to a sample reference locus (m/(1−m)), and the molar ratio in a mixture of a probe query locus to a sample query locus (n/(1−n)), can each be determined using standard methods that are well known to skilled artisans, such as polymerase chain reaction analysis and/or sequencing techniques, such as dideoxysequencing and/or pyrosequencing. In some configurations, aliquots of each mixture can be used for separate pyrosequencing reactions for the reference locus and the query locus.

In some configurations, the molar ratio in a mixture of a reference-query probe reference allele to that of sample reference allele can be from about 1:9 to about 9:1, from about 1:10 to about 10:1, from about 1:15 to about 15:1, or from about 1:20 to about 20:1.

In various embodiments, a sample can comprise a nucleic acid from any source of genetic material, such as any organism, cell, or virus. In some aspects, a sample can comprise, without limitation, DNA of an animal such as nuclear DNA of a vertebrate such as a rodent (e.g., a mouse such as a transgenic or "knock-out" mouse) or a human. Other organisms and viruses which can be analyzed using the methods set forth herein include any plant, insect, worm, eukaryotic microorganism or prokaryotic microorganism or any nucleic acid-containing organelle, such as a mitochondrion, a chloroplast or a ribosome. In some configurations, the present methods can be more rapid, more accurate, and/or simpler to execute than other methods commonly used by skilled artisans for determining copy number, such as Southern Blot or Polymerase Chain Reaction.

In some configurations, a sample reference locus can be a haploinsufficient locus, such as, without limitation, a human gene in which a heterozygous individual displays a phenotype. While any haploinsufficient locus can be used as a reference locus in the present methods, some haploinsufficient genetic loci that can be used as a reference locus include Notch2, SRY, Pax1, GATA4, mel-18, Phox2a, Phox2b, E2f2, FBN1, Tbx5, SHOX and FGFR2.

In some aspects, a sample can comprise, without limitation, nuclear DNA of mammalian cell, such as, for example, DNA of a stem cell such as an embryonic stem (ES) cell that has been transformed or transfected with exogenous DNA. In addition, the methods can be used to determine if the exogenous DNA is incorporated into the cell's genome by homologous recombination.

Various aspects of the present teachings also include the disclosure of a reference-query coupled probe. Such a probe comprises a contiguous nucleobase polymer comprising a reference locus comprising a probe reference allele; and a probe query locus comprising a probe query allele. In various configurations, the probe reference allele can include a probe reference SNP allele, and the probe query allele can comprise a probe query SNP allele. The present teachings further comprise a mixture comprising a biological sample, and a reference-query probe as described above.

BRIEF DESCRIPTION OF THE DRAWINGS

FIG. 8A presents refined screening of 32 ES cells. FIG. 8B demonstrates confirmation by Southern blot of a Kpn 1 digestion of genomic DNAs that all HR candidates identified in FIG. 8a contain the WT allele (6 kb) and the targeted allele (4.6 kb).

FIG. 9A illustrates the Notch2-Pgk1 probe with SNPs introduced to differentiate from the genomic counterparts. FIG. 9B presents an example of a readout (pyrogram) from a Biotage PSQ96-MA machine. The m/(1−m) value was plotted against n/(1−n) (FIG. 9C) indicating that there is one copy of Pgk1. As shown in FIG. 9D, RQPS accurately assigns gender by determining the copy number of the X-linked Pgk1 gene. A statistical analysis of k-values from 18 animals tested demonstrates the robustness of RQPS (FIG. 9e). A slope of k=3.1 was obtained during DNA analysis because three copies of exon 30 were present as expected and the reference allele is haploid (where t=k) (FIG.E, FIG. 9F).

DETAILED DESCRIPTION

The present inventors provide herein methods of determining the molar ratio of a query locus to a reference locus in a sample. In various embodiments, these methods comprise forming either a single mixture or a first mixture and at least one second mixture, each mixture comprising: a) a reference-query coupled probe comprising a nucleobase polymer comprising i) a probe reference locus comprising a probe reference allele, and ii) a probe query locus comprising a probe query allele, and b) a sample comprising i) a sample reference locus comprising a sample reference allele and ii) 0 or greater copies of a sample query locus comprising a sample query allele. In methods comprising two or more mixtures, the reference-query coupled probe and the sample reference locus have a first concentration ratio in a first mixture, and the reference-query coupled probe and the sample reference locus have at least one second concentration ratio in at least one second mixture.

As used herein, the term "allele" refers to a form of a genetic locus that has a sequence difference with another form of the same genetic locus. As used herein, the terms "sample reference allele" and "probe reference allele" refer to sequences comprised by a sample reference locus and a probe reference locus, respectively, which are nearly, but not entirely, identical in sequence. Similarly, a "sample query allele" and a "probe query allele" refer to sequences comprised by a sample query locus and a probe query locus, respectively, which are nearly, but not entirely, identical in sequence. A "sample reference SNP" and a "probe reference SNP," as used herein, refer to a site within a reference sequence that differs by single nucleotide (or nucleobase) between a sample reference sequence and a probe reference sequence. Similarly, a "sample query SNP" and a "probe query SNP," as used herein, refer to a site within a query sequence that differs by single nucleotide (or nucleobase) between a sample query sequence and a probe query sequence.

In various configurations, the present methods include determining, for one or more mixtures, a) the amount of probe reference allele as a fraction of total reference allele (m) and b) the amount of probe query allele as a fraction of total query allele (n). As used herein, "amount" refers to molar amount, unless the context indicates otherwise. In some configurations, the methods can further comprise calculating the molar ratio of the sample query allele to the sample reference allele. In various aspects, calculating the molar ratio between a sample reference locus and a sample query locus can comprise determining the value of m/(1−m) and n/(1−n) for each mixture. In various configurations, each m and n can be determined using pyrosequencing or any other method of quantifying allelic compositions known to skilled artisans.

Figure 1:
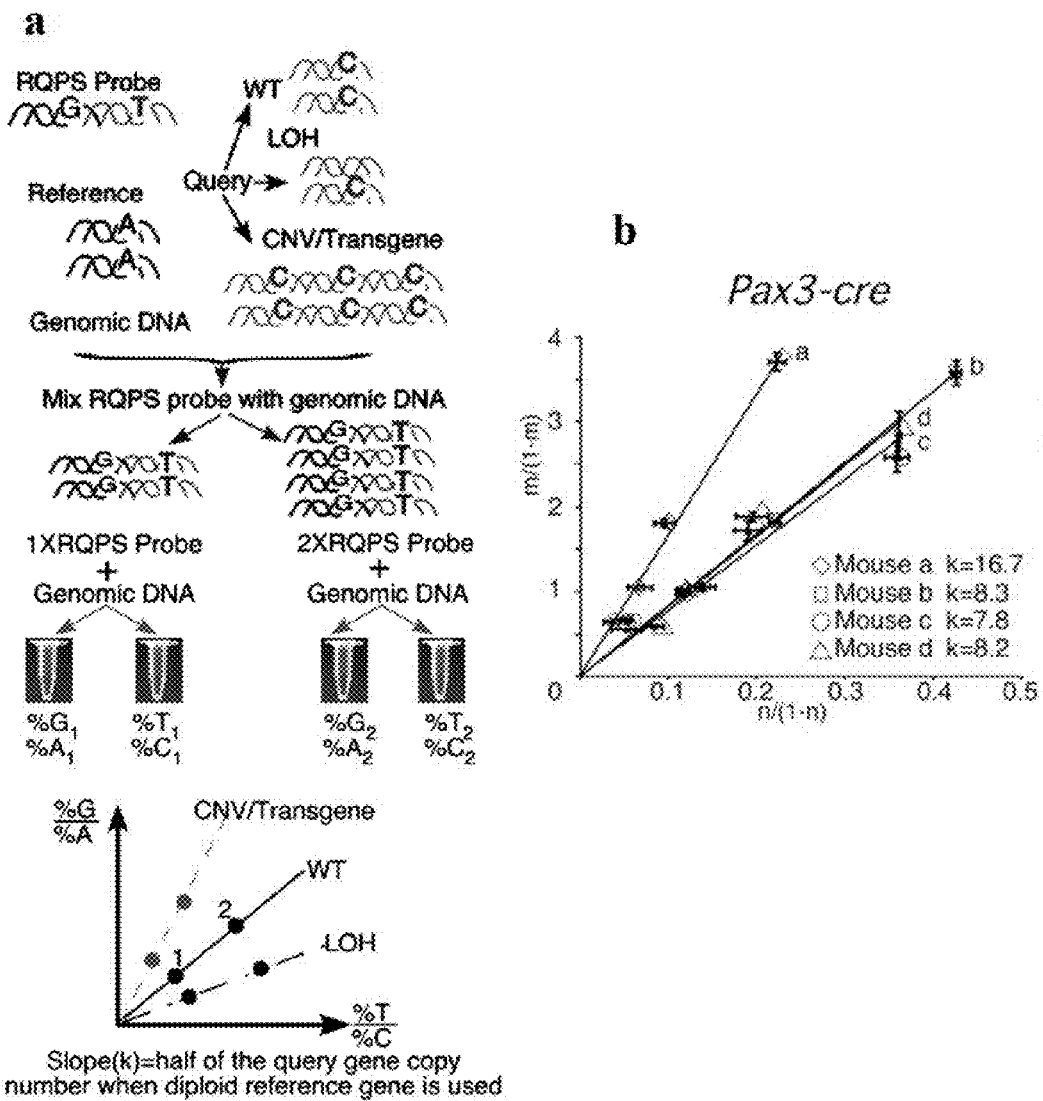
FIG. 1 illustrates method for estimation of gene copy numbers using Reference Query Pyrosequencing (RQPS) (FIG. 1a), as well as actual results used to determine gender of mice (FIG. 1b).

FIG. 1a provides a schematic illustration of Reference Query Pyrosequencing (RQPS). In this method, one or more mixtures are formed, each comprising an RQPS probe and a sample comprising a nucleobase polymer such as a nucleic acid, such as, for example, genomic DNA. The RQPS probe comprises a nucleobase polymer (such as an oligonucleotide) comprising a probe query sequence linked to a probe reference sequence. The probe query sequence and the probe reference sequence are each identical to a corresponding sequence present (or potentially present) in the sample nucleic acid, except that each probe sequence contains an allelic difference with the corresponding sample sequence. As illustrated, an allelic difference can be an artificial SNP comprised by the probe (G and T for the probe reference SNP and probe query SNP, respectively in this illustrative diagram). In some cases, two or more mixtures can be formed, with different molar ratios between the probe and the sample sequences. Molar ratios between a probe and sample can be in a range suited to the detection system used, such as a molar ratio of probe:sample of from about 1:9 to about 9:1. For each mixture, the molar ratio of the probe reference allele (for example, an artificial SNP such as a G nucleobase) to the sample reference allele (for example, an A nucleobase at a corresponding sample sequence), and the molar ratio of the probe query allele (for example, an artificial SNP such as a T nucleobase) to the sample SNP (for example, a C nucleobase at the corresponding sample sequence) can be measured by any method known to skilled artisans, such as quantitative pyrosequencing. The ratio of the sample query allele to the sample reference allele can be determined from these measurements. For example, if the sample comprises genomic DNA, and the sample reference allele and the sample query allele are each comprised by a diploid locus, then % G/% A=% T/% C (wild type, WT in the diagram). If one copy of the sample query locus is lost, then % G/% A will be less than % T/% C (loss of homozygosity, LOH in the diagram). If the sample comprises multiple copies of the sample query locus, then % G/% A will be greater than % T/% C. T and G are used here to represent exemplary nucleobases of a probe query SNP and a probe reference SNP, respectively; C and A are used here to represent exemplary nucleobases of a sample query SNP and a sample reference SNP, respectively. However, SNPs can be any of the four bases.

In some configurations, determining molar ratio of a sample reference locus to a sample query locus for 2 or more mixtures can comprise plotting data points of (n/(1−n)) against (m/(1−m) for each mixture, and fitting a line to the data points. The slope of the line (which can be rounded to a whole number or a ratio of small integers), is typically, after rounding, an integer or a ratio of small integers such as, for example $\frac{1}{2}$, $\frac{1}{3}$, $\frac{2}{3}$, $\frac{1}{4}$, $\frac{1}{5}$, $\frac{3}{4}$, $\frac{3}{5}$, $\frac{3}{2}$, $\frac{5}{2}$, 1, 2, 3, 4, 5, 6, 7, 8, 9, or 10. In some configurations, the slope can equal the molar ratio of the query locus to the reference locus in the sample. In some aspects, copy number of the sample query locus can be determined if the copy number of the sample reference is known. For example, if the reference locus is known to be a homozygous diploid locus, and the slope of the line is about 2, then it can be concluded that the sample contains 4 copies of the query locus. Determinations of query locus copy number can be achieved using a single mixture or a plurality of mixtures. As used herein, "plotting" and "fitting" a line can comprise preparing a graph on paper or on a digital computer with a visual display, and can also comprise calculating a value of a "slope" without any actual graph or visual display, with or without the aid of a computer or other calculating device.

In some aspects, a sample reference allele can comprise a sample reference SNP allele, a sample query allele can comprise a sample query SNP allele, a probe reference allele can comprise a probe reference SNP allele, and a probe query allele can comprise a probe query SNP allele. In some configurations, one or both SNP alleles comprised by the reference-query probe can each be an artificial SNP allele. An artificial SNP allele can be included in a reference-query probe using any strategy known to skilled artisans, such as molecular biological techniques such as PCR, site-directed mutagenesis and recombinant DNA cloning methods, as well as organic synthesis methods.

In various configurations, a reference-query probe can be a nucleobase polymer comprising a reference sequence fused to a query sequence, wherein each of which comprises an allelic difference with a sequence comprised by the sample. An allelic difference between a probe sequence and a sample sequence can be, for example, a single base difference, such as a single nucleotide polymorphism (SNP). For both a reference locus and a query locus, a reference-query probe need only comprise sufficient sequence information to be distinct from corresponding regions in a sample. For example, if a probe reference locus and a sample reference locus differ by only a single base, the reference-query probe can include a sequence of at least 8, at least 9, or at least 10 nucleotides (or nucleobases) identical to a corresponding sample reference locus sequence, except for a single base (a SNP allele). Similarly, if a probe query locus and a sample query locus differ by only a single base, the reference-query probe can include a sequence of at least 8, at least 9, or at least 10 nucleotides (or nucleobases) identical to a corresponding sample query locus sequence, except for a single base (a SNP allele). Furthermore, a reference-query probe, as well as both the reference locus and the query locus comprised by the probe, can be of any length. In addition, the present methods can be used when a reference-query probe and a sample contain an allelic difference other than alternative SNP alleles, such as, without limitation, an insertion, an inversion, or a deletion. In various configurations, a reference-query probe can be a nucleobase polymer such as a oligonucleotide or a vector comprising a probe reference sequence and a probe query sequence. Without limitation, a vector of these configurations can be a plasmid vector or a virus vector.

In various aspects, a SNP allele comprised by either a reference locus or a query locus of a reference-query probe can be an artificial SNP allele. In some configurations, a database or table of known SNP alleles can be searched to determine if a sequence considered for inclusion in a reference-query probe already includes a SNP; in some configurations, a position that does not have any known SNP can be used to generate a nucleobase polymer comprising an artificial SNP. An example of such a database is the NCB1 SNP database, which can be searched on the internet at http://www.ncbi.nlm.nih.gov/projects/SNP/.

In various configurations, a sample query locus can be present in an unknown number of copies, such as 0 copies, 1 copy, 2 copies, or greater. There is, in principle, no limit to the number of copies of a query locus in a sample that can be determined using the methods of the present teachings. Hence, in various configurations, the methods can be used, for example, to determine the copy number of a transgene in a transgenic organism such as a transgenic mouse, or to establish if exogenous DNA introduced into a stem cell is incorporated in the stem cell's genome by homologous or illegitimate recombination.

amount of probe reference allele as a fraction of total reference allele (m) and the amount of probe query allele as a fraction of total query allele (n) in a mixture can be achieved in a single tube using pyrosequencing, for example, by use of multiplex pyrosequencing (Pourmand, N., Nucleic Acids Res. 30, e31, 2002). In various configurations, primers that can be used in a pyrosequencing analysis can include a biotinylated primer. As is well understood by skilled artisans, a determination for a mixture of a molar ratio of a probe locus to a corresponding sample locus can be used to determine the molar fraction of the probe locus to the total locus (or vice versa) in the mixture, by simple mathematical relationships. For example, if a probe reference locus and a sample reference locus are in a molar ratio of 3:1, then the molar fraction of the probe locus in the mixture is $3/4=0.75$.

In a hypothetical "proof of principle" example, assume for each of two mixtures, (mixture 1 and mixture 2) that a sample is genomic DNA comprising a sample reference locus at a concentration of 10 nM and sample query locus at a concentration or 5 nM. Mixture 1 further comprises a probe comprising a probe reference locus and a probe query locus, each at a concentration of 3 nM. Mixture 2 further comprises a probe comprising a probe reference locus and a probe query locus, each at a concentration of 8 nM. Hypothetical values for m, m/(1−m), n and n/(1−n) are illustrated in the following table.

| Mixture 1 | Reference | Query | Mixture 2 | Reference | Query |
|---|---|---|---|---|---|
| Sample (S) | 10 nM | 5 nM | Sample (S) | 10 nM | 5 nM |
| Probe1 (P1) | 3 nM | 3 nM | Probe2 (P2) | 8 nM | 8 nM |
| S + P1 | 13 nM | 8 nM | S + P2 | 18 nM | 13 nM |
| P1/(S + P1) (i.e., m, pyrosequencing readout for probe reference SNP) | 0.230769 | | P2/(S + P2) | 0.444444 | |
| n (pyrosequencing readout for probe query SNP) | | 0.375 | | | 0.615385 |
| m/(1 − m) (i.e. P1/S) | 0.3 | | | 0.8 | |
| n/(1 − n) (i.e, P1/S) | | 0.6 | | | 1.6 |

In some aspects of the present teachings, the molar ratio in a mixture of a probe reference locus to a sample reference locus, and the molar ratio in a mixture of a probe query locus to a sample query locus, can each be determined using standard methods that are well known to skilled artisans, such as polymerase chain reaction analysis and/or sequencing techniques, such as dideoxysequencing and/or pyrosequencing (Ronaghi, M., et al., Biotechniques 25: 876-878, 1998; Ronaghi, M., et al., Anal. Biochem. 267: 65-71, 1999; Guo, D. C., et al., Methods Mol. Biol. 373: 576-62, 2007; Royo, J. L., et al., Nature Protocol 2: 1734-1739, 2007). In some configurations, aliquots of each mixture can be used for separate pyrosequencing mixtures for the reference locus and the query locus. En some configurations, the measurement of the A two dimensional plot (or calculation) of m/(1−m) vs. n/(1−n) yields a line with slope=0.5, indicating that the sample query locus is at half the concentration of the sample reference locus. If the reference locus is known to be diploid locus, then one can conclude that the query locus is a haploid.

In another hypothetical "proof of principle" example, assume for each of two mixtures, (mixture 1 and mixture 2) that a sample is genomic DNA comprising a sample reference locus at a concentration of 10 nM and sample query locus at a concentration of 20 nM. Mixture 1 further comprises a probe comprising a probe reference locus and a probe query locus, at a concentration of 5 nM. Mixture 2 comprises the probe at a concentration of 12 nM. Hypothetical values for m/(1−m) and n/(1−n) are illustrated in the following table.

| Mixture 1 | Reference | Query | Mixture 2 | Reference | Query |
|---|---|---|---|---|---|
| Sample (S) | 10 nM | 20 nM | Sample (S) | 10 nM | 20 nM |
| Probe1 (P1) | 5 nM | 5 nM | Probe2 (P2) | 12 nM | 12 nM |
| S + P1 | 15 nM | 25 nM | S + P2 | 22 nM | 32 nM |
| P1/(S + P1) (i.e., m, pyrosequencing readout for probe reference SNP) | 0.333333 | | P2/(S + P2) | 0.545454 | |
| n (pyrosequencing readout for probe query SNP) | | 0.2 | | | 0.375 |
| m/(1 − m) | 0.5 | | | 1.2 | |
| n/(1 − n) | | 0.25 | | | 0.6 |

A two dimensional plot (or calculation) of (m/(1−m)) vs. (n/(1−n)) leads to a slope=2, indicating that the sample query locus is at twice the concentration of the sample reference locus. If the sample reference locus is known to be a haploid locus, then one can conclude that the sample query locus is present in two copies.

In a third hypothetical "proof of principle" example, assume for a mixture that a sample is genomic DNA comprising a sample reference locus at a concentration of 10 nM and sample query locus at a concentration of 30 nM. The mixture further comprises a probe comprising a probe reference locus and a probe query locus, each at a concentration of 5 nM.

| | Reference | Query |
|---|---|---|
| Sample (S) | 10 nM | 30 nM |
| Probe1 (P1) | 5 nM | 5 nM |
| S + P1 | 15 nM | 35 nM |
| P1/(S + P1) (i.e., m, pyrosequencing readout for probe reference SNP) | 0.333333 | |
| n (pyrosequencing readout for probe query SNP) | | 0.142857 |
| m/(1 − m) | 0.5 | |
| n/(1 − n) | | 0.166667 |

If the origin is considered a data point for calculation purposes, a two dimensional plot (or calculation) of m/(1−m) vs. n/(1−n) yields a line of slope=3, indicating that the sample query locus is at a concentration three times that of the sample reference locus. If the sample reference locus is known to be haploid locus, then one can conclude that the query locus is present in three copies.

In a fourth hypothetical "proof of principle" example, assume that a mixture contains a genomic DNA sample with a haploid sample reference locus and an unknown number of copies of a sample query locus. Two mixtures are formed, each comprising genomic DNA in which the reference locus is present at a concentration of approximately 10 nM. A first mixture includes a probe at a concentration of about 5 nM. A second mixture includes a probe at a concentration of about 10 nM. Molar ratios of the probe and sample loci are determined using a standard method such as pyrosequencing. Hypothetical results are shown in the following table:

| Mixture 1 | Reference | Query | Mixture 2 | Reference | Query |
|---|---|---|---|---|---|
| P1/(S + P1) (i.e., m, pyrosequencing readout for probe reference SNP) | 0.30 | | P2/(S + P2) | 0.46 | |
| n (pyrosequencing readout for probe query SNP) | | 0.18 | | | 0.3 |
| m/(1 − m) | 0.43 | | | 0.85 | |
| n/(1 − n) | | 0.22 | | | 0.43 |

A plot of m/(1−m) vs. n/(1−n) yields a line of slope 2, indicating that the sample genome contains 2 copies of the sample query locus.

Although the present methods can be used with mixtures comprising a reference-query probe and a sample at virtually any molar ratio, in some embodiments, the molar ratio of a reference-query probe reference allele to that of sample reference allele in a mixture can be from about 1:9 to about 9:1. Hence, in various configurations, the molar ratio of a reference-query probe reference allele to that of sample reference allele in a mixture can be, without limitation, in a range of from about 1:20 to about 20:1, from about 1:15 to about 15:1, from about 1:10 to about 10:1, from about 1:8 to about 8:1, from about 1:7 to about 7:1, from about 1:6 to about 6:1, from about 1:5 to about 5:1, or from about 1:4 to about 4:1. In addition, when two or more mixtures are used with different concentrations of probe and sample, either the sample concentration can vary with respect to the probe concentration, or vice versa.

In various embodiments, a sample can comprise a nucleic acid from any source of genetic material, such as any organism, cell, virus, or a synthetic source. In some aspects, a sample can comprise, without limitation, DNA of an animal such as nuclear or mitochondrial DNA of a vertebrate, including a bird, a reptile, an amphibian, a fish or mammal, such as a rodent (e.g., a mouse such as a transgenic or "knock-out" mouse), a companion animal, a farm animal or a human. Other organisms which can be analyzed for copy number of a genetic locus using the methods set forth herein include a plant (such as *Arabidopsis thaliana*), an insect (e.g., *Drosophila melanogaster*) a worm (such as *Caenorhabditis elegans*) or a microorganism e.g., a bacterium such as *Escherichia coli* or a yeast such as *Saccharomyces cerevisiae*, or a plant such as, for example, a crop plant (such as corn, wheat, soybean, rapeseed, or rye).

Although any genetic locus believed to be sufficiently stable in an organism or species can be used as a reference locus, in some configurations, a sample locus can be a haploinsufficient locus. As used herein, a haploinsufficient locus refers to a gene in which a heterozygous or hemizygous individual sports a phenotype that can be distinguished from that of a homozygous individual. Without being limited by theory, the inventors believe that use of a haploinsufficient genetic locus as a reference locus can help ensure that the reference locus is a diploid locus. In some configurations, if the reference locus is known to be a male-specific, haploid locus such as SRY (Berta, P., et al., Nature 348: 448-450, 1990) or Pax1 (Wilm, B., et al., Proc. Nat'l Acad. Sci. USA 95: 8692-8697, 1998), or a haploinsufficient locus, and the molar ratio of the query locus to the reference locus in the sample is determined, the copy number of the query locus can be determined on the basis of the copy number of the sample reference locus as inferred from the phenotype of the original source of the sample. While virtually any haploinsufficient genetic locus can be used as a reference locus; some non-limiting examples of haploinsufficient genetic loci which can be used as a reference locus for the present methods include Notch-2 (McDaniell, R., et al., Am. J Hum. Genet. 79: 169-173, 2006), GATA4 (Pehlivan, T. et al., Amer. J. Med. Genet. 83: 201-206, 1999), Phox2a (Wrobel, L. J., et al., Neuroscience 145: 384-392, 2007, Phox2b (Cross, S. H., et al., Human Mol. Genetics 13: 1433-1439, 2004), FBN1 (Mátyás, G., et al., Human Genetics 122: 23-32, 2007), Tbx5 (Georges, R., et al., Mol. Cell Biol. 28: 4052-4067, 2008), and FGFR2 (Tsukuno, M., et al., J. Craniofac. Genet. Dev. Biol. 19: 183-188, 1999). Other non-limiting examples of haploinsufficient genetic loci which can be used as reference loci can be found in published resources, such as a database freely available on the internet, at the NCBI Mendelian Inheritance in Man website (OMIM) at http://www.ncbi.nlm.nih.gov/sites/entrez.

In some embodiments, the methods can be used diagnostically. In a non-limiting example, the methods can be used to determine if cells of a cancerous tumor include an amplified oncogene (e.g., Watson, M. A., et al., Oncogene 16: 817-824, 1998; Brodeur, G. M., Adv. Pediatr. 34: 1-44, 1987; Baldus, C. D., et al., British J. Haematol. 137: 387-400, 2007).

In some embodiments, the methods can be used to determine the status of a patient receiving a genetic therapy. For example, in a patient receiving a vector comprising a therapeutic gene (see, e.g., Sand, M. S. et al., Acta Paediatr. Suppl. 97: 22-27, 2008; Ponder, K. P., et al., Expert Opinion Biol. Ther. 7: 1333-1345, 2007; Corbo, J. C., Expert Opinion Biol. Ther. 8: 599-608, 2008; Ponder, K. P., Curr. Opinion Hematol. 13: 301-307, 2006; Sands, M. S. et al., Mol. Ther. 13: 839-849, 2006), methods of the present teachings can be used to monitor the status of the therapeutic gene, for example in a blood or biopsy sample.

In some embodiments, the methods can be used to examine and quantify evolutionary changes. For example, the methods set forth herein can be used to determine copy number variation and evolution in humans and chimpanzees (Hallast, P., et al., BMC Evol. Biol. 8: 195) or cold tolerant grasses (Sandve, S. R., BMC Evol. Biol. 8: 245).

In some aspects, a sample can comprise, without limitation, nuclear DNA of mammalian cell, such as, for example, DNA of an embryonic stem (ES) cell that has been transformed or transfected with exogenous DNA. In addition, the methods can be used to determine if the exogenous DNA is incorporated into the cell's genome by homologous recombination.

Various aspects of the present teachings also include the disclosure of a reference-query coupled probe. Such a probe comprises a nucleobase polymer comprising a reference locus comprising a probe reference allele; and a probe query locus comprising a probe query allele. In various configurations, the probe reference allele can include a probe reference SNP allele, and the probe query allele can comprise a probe query SNP allele. In various configurations, a probe comprising the sequences can further comprise a vector such as a plasmid or virus.

EXAMPLES

The following Examples are intended to be illustrative of various aspects of the present teachings and are not intended to be limiting of any aspect. While some of examples may include conclusions about the way the invention may function, the inventors do not intend to be bound by those conclusions, but put them forth only as possible explanations. Unless indicated by use of past tense, presentation of an example does not imply that an experiment or procedure was, or was not, conducted, or that results were, or were not, actually obtained. The methods and compositions described herein utilize laboratory techniques well known to skilled artisans, and can be found in laboratory manuals such as Sambrook, J., et al., Molecular Cloning: A Laboratory Manual, 3rd ed. Cold. Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Ausubel, F. M., et al., ed., Current Protocols in Molecular Biology, Wiley Interscience, 2003; Nagy, A., et al., Manipulating the Mouse Embryo: A Laboratory Manual (Third Edition), Cold Spring Harbor Laboratory Press, Cold Spring Harbor, N.Y., 2003. As used in the description and the appended claims, the singular forms "a", "an" and "the" are intended to include the plural forms as well, unless the context indicates otherwise.

In these examples, the inventors demonstrate determining copy number of a genetic locus. In these examples, PCR and pyrosequencing primers designed using the Pyrosequencing Assay Design Software (Biotage, Uppsala, Sweden) worked under the same experimental conditions without any failure. Only if the transgene copy numbers are unusually high will more then two data points be necessary to attain SNP ratios between 10% to 90%. When two dilutions, four wells per sample (one for a reference SNP and one for a query SNP in each dilution) are used, 24 samples can be processed in a 96-well plate.

Experiments presented in the examples utilize the following materials and methods: Generation of targeting constructs The four targeting constructs used in the experiments described herein are: (1) Notch1-cre and (2) Notch1-CreERT2, in which the Notch1 intracellular domain is replaced with Cre recombinase and tamoxifen-inducible CreERT2 fusion protein, respectively; (3) Notch2-cre and (4) N2-N1, in which the Notch2 intracellular domain is replaced with Cre recombinase and the intracellular domain of Notch1, respectively. The details of constructing the N1-CreERT2 are provided in FIG. 4 to explain how SNPs were simultaneously incorporated into targeting construct through BAC recombineering.

Figure 4:
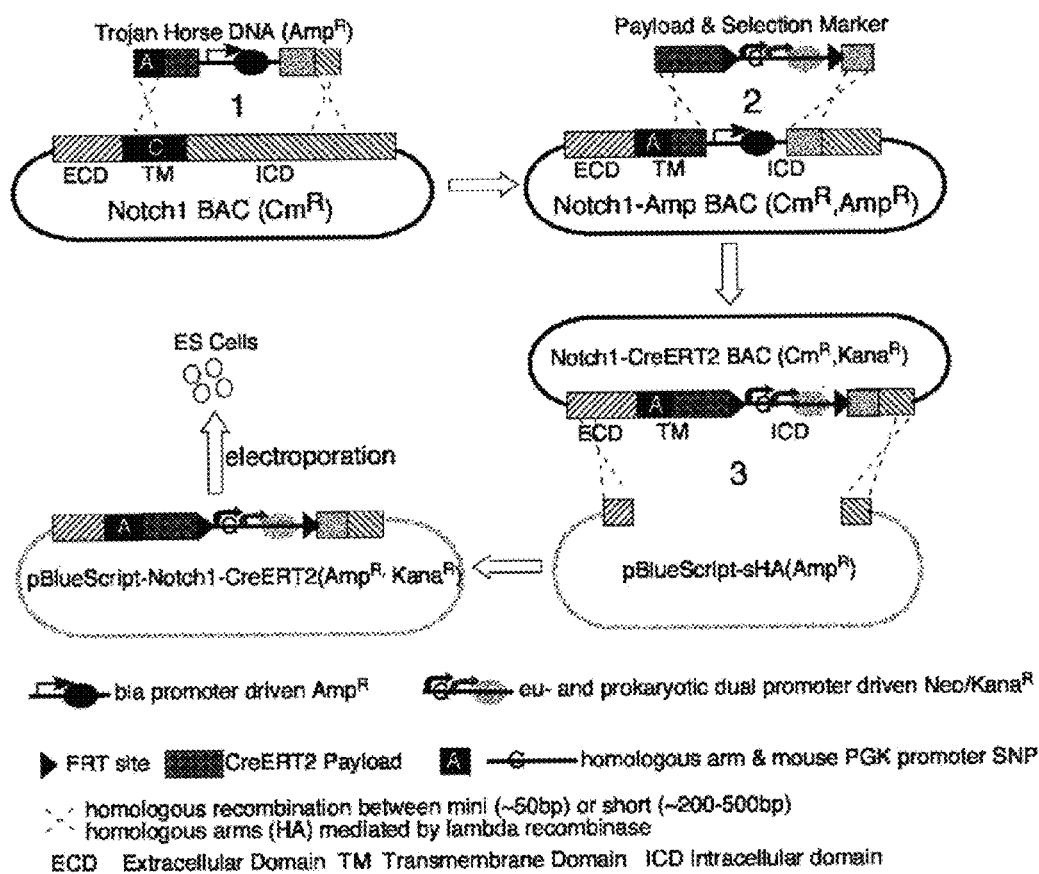
FIG. 4. illustrates a method of introducing artificial SNPs into a gene targeting construct using N1-CreERT2.

In brief, a 6×myc-tagged CreERT2 fusion gene was First cloned in front of a frt-flanked neomycin selection cassette, whose expression is under the control of both a mouse PGK promoter and an E. coli EM7 promoter; an artificial SNP was introduced into the mouse PGK for pyroscreening. Next, PCR, using pBlueScript® (Stratagene) as a template, was used to amplify a fragment including the blastidin promoter driving ampicillin resistance gene. Two pairs of flanking mini-homology arms (HA) were added by subsequent rounds of PCR. The outer mini-HAs mediate the integration of the fragment into Notch1 BAC; the inner mini-HAs mediate subsequent replacement of ampicillin cassette with the payload (6×Myc-CreERT2Frt; PGKEM7-Neo cassette). In addition, a SNP was inserted into the outer mini-HAs (FIG. 4). This strategy facilitates the insertion of large DNA fragments by inserting the mini-HR into the BAC circumventing the need to amplify the payload in order to introduce homology arms into it. Finally, the CreERT2FrtNeo cassette with 4.8 Kb upstream and 2.2 kb downstream of flanking BAC DNA was recombined into pBluescript plasmid by traditional BAC retrieval methods.

ES Cell Electroporation

ES cell electroporation and selection was performed by Siteman Cancer Center ES Core Facility at Washington. University in St. Louis (http://escore.im.wustl.edu). ~40 μg of linearized targeting construct was electroporated into either 129-derived SSC10 ES cells (for N1-cre) or C57BL6-derived B6/BLU ES cells (the other three constructs). Neomycin resistant clones were selected by the Core Facility and expanded by the investigators for further screening.

Nucleic Acid Purification

Genomic DNA from ES cells and mouse tissue was purified using routine methods. Total RNA from mouse tissues was purified using an RNeasy Mini Kit (Qiagen) and residual DNA contamination was removed by on-column treatment with RNase-free DNase Set (Qiagen, Germany). cDNA first strand was reverse-transcribed with random hexamer and Superscript II Reverse Transcriptase (Invitrogen, Carlsbad, Calif.).

PCR and Southern Blot Screening of ES Cells

Nested PCR was used for the screening of ES cells with long homology arms. Purified BAC DNA containing a targeting construct was diluted with wild type mouse genomic DNA and used as positive control for the optimization of PCR conditions. PCR primers used and the expected size of the PCR products are listed in Table 2. Southern blot was done using routine procedure with α-P32-dCTP labeled probes (Amersham).

Pyrosequencing

The three-primer PCR reaction system was employed for the amplification of the DNA fragment containing SNP of and all primers were designed using Pyrosequencing Assay Design Software (Biotage, Sweden; Table 3). The PCR reaction mixtures included: 2 μl DNA template, 12.5 μl Bullseye Taq DNA Polymerase Mix (Midsci, St. Louis, Mo.), 1 μl un-tailed gene-specific primer, 0.2 ul tailed gene-specific primer, 0.8 μl universal biotin-labeled primer (all at a concentration of 5 μM) and 8 ul distilled water. PCR conditions were 95° C. for 8 minutes followed by 40 cycles with denaturation at 95° C. for 30 sec, annealing at 60° C. for 30 sec, and elongation at 72° C. for 30 sec.

A Pyrosequencing Vacuum Prep Tool was used to obtain single-stranded biotinylated PCR products immobilized on streptavidin-coated sepharose beads: for each reaction, 40 μl Binding Buffer (10 mM Tris-HCl, 2M NaCl, 1 mM EDTA, 0.1% Tween 20, pH7.6), 20 μl high purity water, and 3 μl. Streptavidin Sepharose™ High Performance beads were mixed together with 20 μl PCR product for 10 minutes at room temperature using an Eppendorf Thermomixer. After immobilization, vacuum was applied to the Prep Tool and the template was captured on filter probes. The non-biotinylated template was then denatured by alkali treatment and removed by washing for 5 secs in 70% EtOH for 5 secs, 0.2M NaOH denaturation solution for 5 sec and 10 mM Tris-Acetate Washing Buffer (pH7.6) for 5 sec. This washing step also neutralized the pH. Next, the vacuum was released and the beads were transferred into a PSQ 96 Plate Low containing the sequencing primer (5 pmol) and 40 μl Annealing Buffer (20 mM Tris-Acetate, 2 mM MgAc$_2$, pH 7.6). The Pyrosequencing reactions were performed using a PSQ96-MA machine (Biotage, Inc.) according to the manufacturers instructions using the Pyro Gold reagent kit (Biotage, Inc). Assays were performed using cyclic enzyme and nucleotide dispensation and analyzed using the SNP Software (Biotage, Inc).

Example 1

This example illustrates using the methods set forth herein to determine the gender of laboratory mice.

Figure 9:
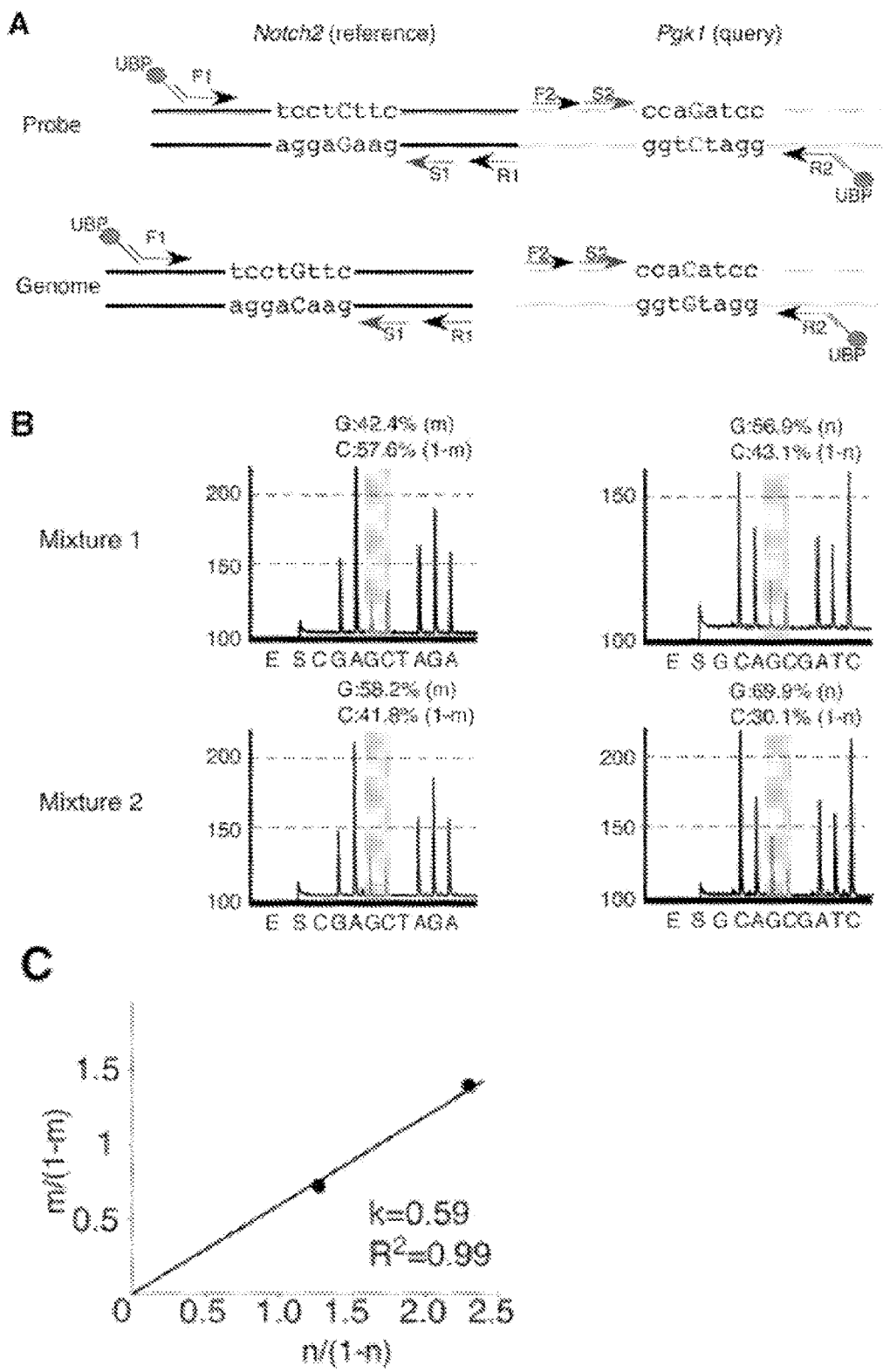
FIG. 9 illustrates RQPS accurately determines gene copy number.
Figure 9:
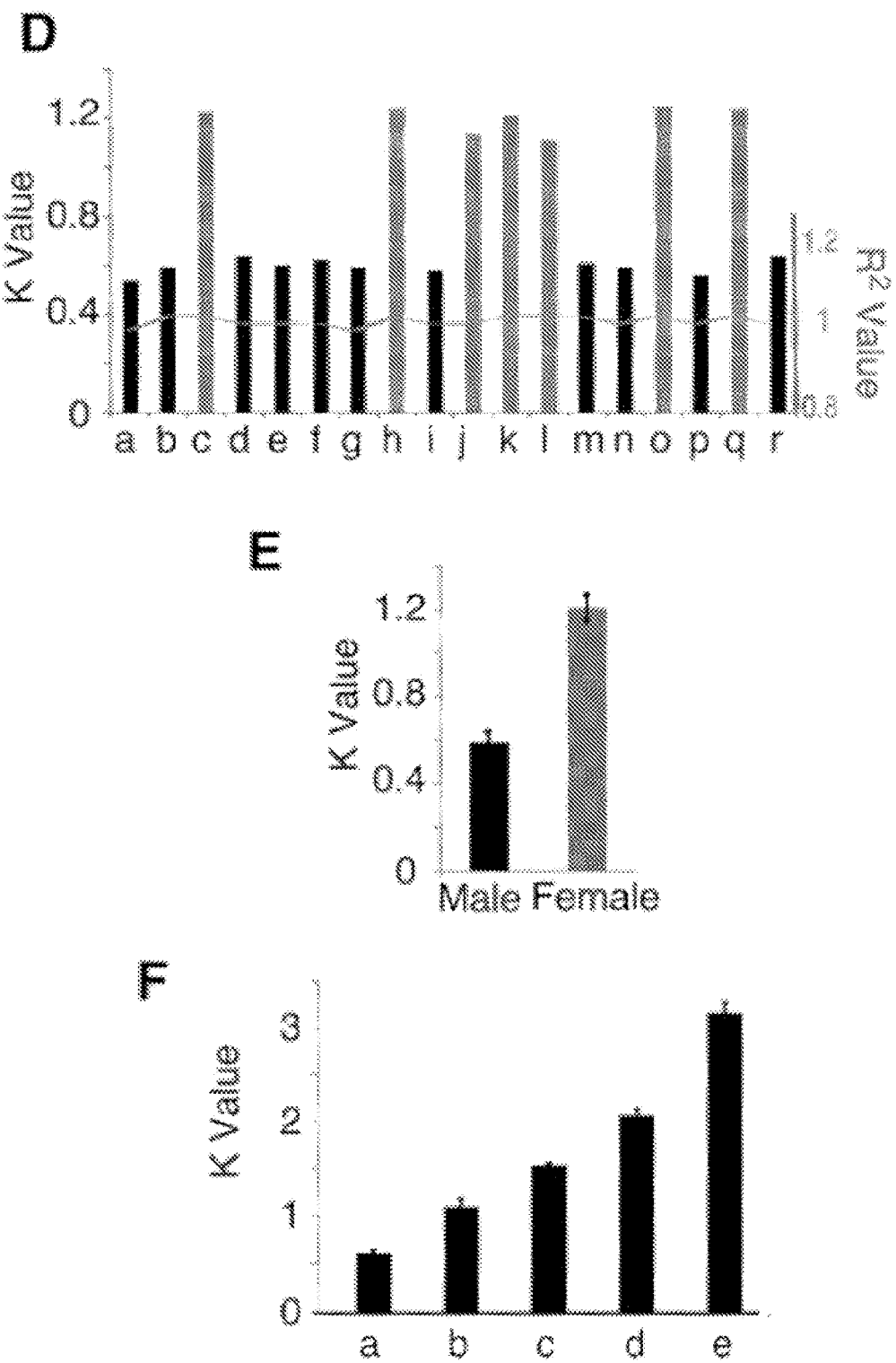

In these experiments, we determined the gender of 18 animals in a blind experiment. In these experiments, mixtures were formed comprising samples of genomic DNA comprising the X-linked phosphoglycerate kinase (PGK) gene and a diploid Notch2 gene, and a probe comprising PGK and Notch2, each with an artificial SNP. We made a plasmid containing a ligated fragment from the Pgk1 promoter (as the query probe) and a fragment from a Notch2 exon (as the reference probe). FIG. 9a illustrates the Notch2-Pgk1 probe with SNPs introduced to differentiate it from the genomic counterparts. In the RQPS probe, the reference Notch2 fragment has a G-to-C SNP while Pgk1 has a C-to-G SNP. The fragment containing the Notch2 SNP was amplified with a three-primer system: (1) the forward tailed primer F1 with a complementary region to (2) the universal biotinylated primer (UBP), and (3) the untailed reverse primer R1. The fragment containing the Pgk1 SNP was amplified with the same UBP primer and two gene-specific primers (untailed forward primer F2 and a tailed reverse primer R2). The biotinylated PCR product was purified with streptavidin-coated Sepharose beads and sequenced with a sequence primer (S1 for Notch2 and S2 for Pgk1, respectively) hybridizing near the desired SNP. Each was mutated to include a single nucleotide variation (SNV).

Two mixtures with different ratios of Notch2-Pgk1 RQPS probe to genomic DNA were prepared and quantitatively pyrosequenced in four reactions per individual, one for each SNV in each mixture. FIG. 9b presents an example of a readout (pyrogram) from a Biotage PSQ96-MA machine. Two probe/genomic DNA mixtures were prepared in this example. Reference and query SNPs were quantified by pyrosequencing of each mixture; the relative ratio is shown. Note that a G, instead of a C, determines the ratio of the RQPS probe in each mixture because the sequencing primer for the Notch2 reference gene binds to the minus strand.

The $m/(1-m)$ value was plotted against $n/(1-n)$ (FIG. 9c). The plot of $m/(1-m)$ against $n/(1-n)$ gives a line that passes (0, 0) with slope $k=0.59$, which indicates that there is one copy of Pgk1 in this mouse and hence it is a male.

The animals were segregated into two groups: one with the slope $k=0.6$ and another with the slope $k=1.2$, consistent with $t=2k$ values of 1.2 for males and 2.4 for females (FIG. 9d, FIG. 9e). As shown in FIG. 9d, RQPS accurately assigns gender by determining the copy number of the X-linked Pgk1 gene. All male mice show a k-value of ~0.6 and all females ~1.2. A statistical analysis of k-values from 18 animals tested demonstrates the robustness of RQPS (FIG. 9e).

We conclude that RQPS correctly determined the gender of all of the animals tested. Our results show that the methods set forth herein can be used to determine gender of mice with high accuracy.

Example 2

This example illustrates using the present methods to measure the copy number of Notch1 intracellular domain in genetically modified as well as wild type mice and further verifies the accuracy of the methods.

To further assess the accuracy of RQPS, the copy number of exon 30 in the Notch1 intracellular domain (N1ICD) was measured in four different transgenic lines with clearly defined copy numbers (Murtaugh, L. C., et al. Proc. Nat'l. Acad. Sci. USA 100: 14920-14925, 2003; Vooijs, M., et al., Development 134:535-544, 2007). The RQPS probe used for this experiment consisted of two short DNA fragments, one from Notch1 exon 23 and another from exon 30, mapping to Notch1 extracellular and intracellular domains, respectively, and fused together to function as reference and query probes. The slopes (k) obtained were ~0.6, 1.1, 1.6, and 2.1 (FIG. 9f), correctly identifying animals with t=1, 2, 3, and 4 copies of exon 30.

This analysis was successfully repeated with additional Notch1 alleles, correctly identifying the number of N1ICD in various genomes. Importantly, in mice containing the N1+/Δ1 allele, which harbors a deletion removing exons 23-30 (Conlon et al. 1995), only one copy of exon 23 is present in the genome. When analyzing N1+/Δ1;Gt(ROSA)26Sor$^{Notch/Notch}$ DNA, a slope of k=3.1 was obtained because three copies of exon 30 were present as expected and the reference allele is haploid (where t=k) (FIG. 9e, FIG. 9f).

As shown in FIG. 9f, RQPS accurately measured the copy number of exon 30 from the Notch1 gene, encoding a part of the Notch1 intracellular domain, in five different lines of mice that are known to have (a) one, (b) two, (c,e) three, and (d) four copies of the NICD1, respectively (FIG. 9f). In these experiments, RQPS was used to determine the copy number of the Notch1 intracellular domain (N1) in four mouse lines A, B, C and D. Because a diploid reference gene was used as a sample reference locus for mouse lines A, B, C and D, the k values were equal to half the copy number of the Notch1 sample query locus. When the N1+/Δ1;Gt(ROSA)26Sor$^{Notch/Notch}$ mouse was used, owing to a deletion removing exon 30 (query) and exon 23 (reference) from one allele (Conlon, R. A., et al., Development 121:1533-1545, 1995), three copies of N1 ICD produced k=3.1. The results for these mouse lines were as follows: A, N1::re in one copy; B, wild type, 2 copies; C, N1+/+N2+/21, 3 copies (in which one copy of the Notch2 intracellular domain was replaced with that of Notch1); D, N1+/+, N2 21/21, 4 copies (in which both copies of Notch2 intracellular domain were replaced with that of Notch1). In mouse line E, N1+/+, N2+/21. Because a haploid reference gene was used as the sample reference locus, the k values equaled the copy number of the Notch1 sample query locus, which was 3.

This example demonstrates that RPQS can be used to determine copy numbers of an exon.

Example 3

This example illustrates using the present methods to measure transgene copy number. This example also illustrates using the present methods to distinguish homozygous from heterozygous pups in transgenic Cre lines.

In these experiments, a probe (Notch2-Cre) was prepared with artificial SNP alleles in the query and reference sequences. Pax3-cre transgenic mice (Li, J., et al., Genesis 26: 162-164, 2000) were chosen for proof-of-principle analysis since the copy number and integration site of this transgene is unknown. As shown in FIG. 1b, we analyzed the zygosity of four male pups by plotting results from four different RQPS probe dilutions for each genomic DNA sample. We observed three lines with a slope k ~8 and one with a slope k ~16. Not only did this method allow us to identify a lone homozygous male (confirmed by multiple rounds of mating these studs with wild type females; FIG. 1b), it simultaneously led to an estimate of the Pax3-Cre transgene copy number in hemizygotes to be roughly 16 (FIG. 1b).

In addition, we confirmed that each mouse having a k value ~0.6 (indicating 1 copy of the PGK gene) was also anatomically male, and each mouse having a k value ~1.2 (indicating 2 copies of the PGK gene) was also anatomically female, demonstrating 100% accuracy in sex determination. Pyrosequencing of each SNP of each mixture was performed in triplicate and the average values were plotted; data points +/− standard deviation are shown. The small standard deviations for each data point indicate that triplicates or duplicates were not necessary to reach the conclusions.

Example 4

This example further illustrates using the present methods to measure transgene copy number and demonstrates that the same Notch2-cre RQPS probe can be used as a universal reagent for all Cre transgenic mice.

Figure 2:
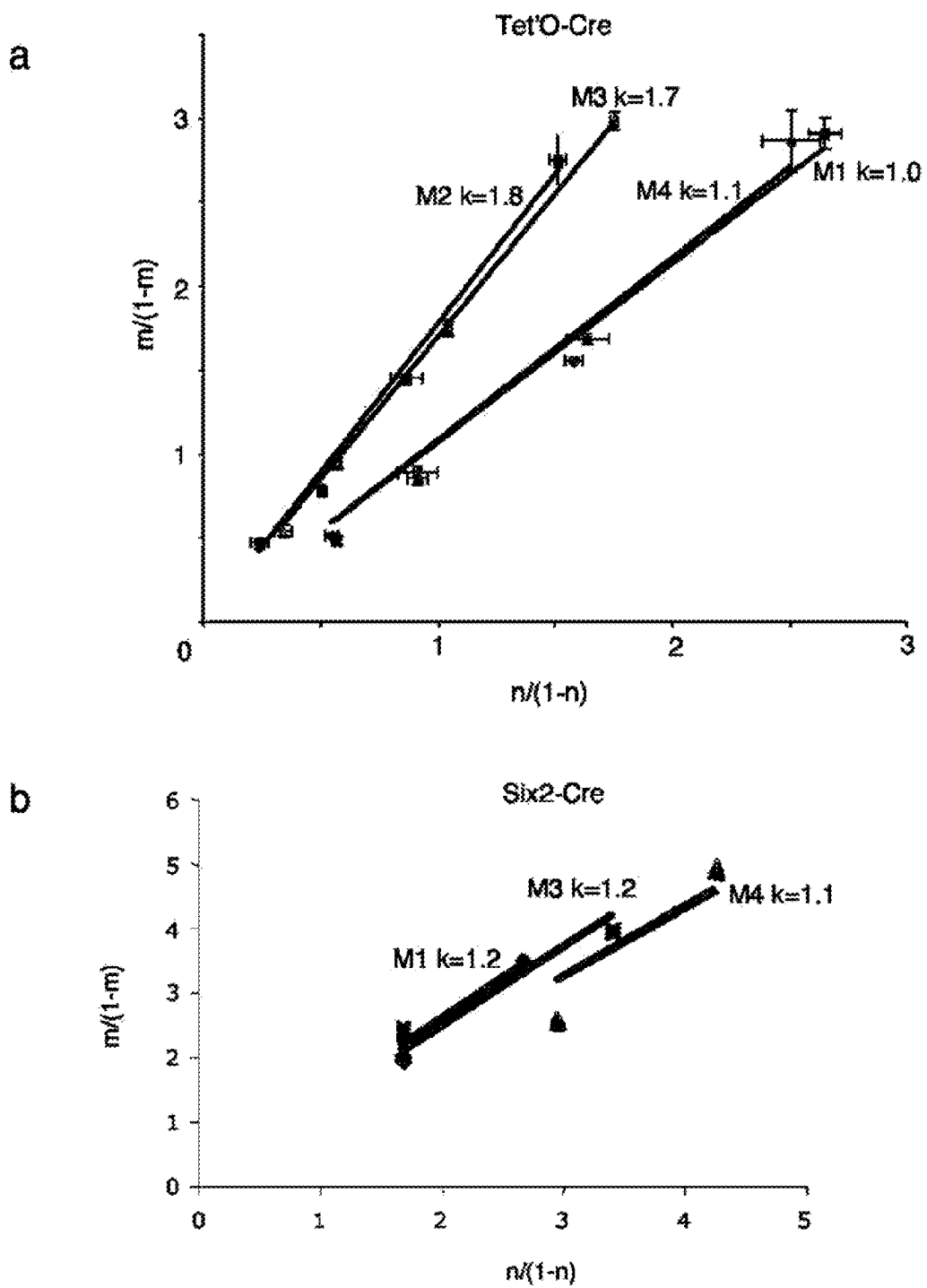
FIG. 2 illustrates determination of transgene copy number measurement using RQPS. RQPS Determined the copy number of the transgenes TetO-Cre (FIG. 2a) and Six2-Cre (FIG. 2b) in Transgenic animals.

Using the same Notch2-cre RQPS probe, we tested the TetO-cre and Six2-Gfp::Cre lines in our colony and determined their copy number to be both 2 in hemizygotes (FIG. 2). In these experiments, the copy number of the Tet-O Cre transgene was measured in 4 animals. Four different mixtures were pyrosequenced for each sample in duplicate. RQPS detected two homozygotes and two heterozygotes, with 2 and 4 copies of the transgene respectively (FIG. 2a).

RQPS was performed on DNA from three heterozygotic Six2-cre transgenic animals (FIG. 2b). In these experiments, two different mixtures were pyrosequenced for each animal, without duplication. The results show that two copies of this transgene exist in each animal.

These results demonstrate that RQPS provides a method for the simultaneous determination of breeder zygosity and copy number.

Example 5

This example illustrates methods of the present teachings adapted for the pre-screening of electroporated ES cells for homologous recombinants.

Figure 3:
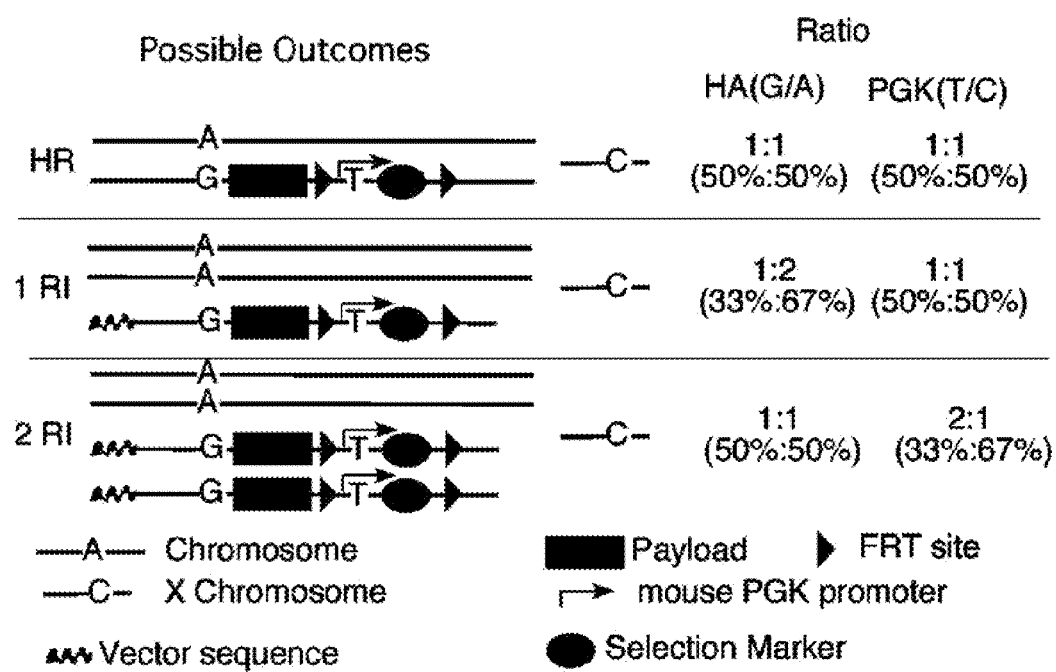
FIG. 3 illustrates RQPS adapted for pre-screening of gene targeted ES cells.

In this example, we introduced two SNPs into a vector: one on the homology arm (the HA SNP), roughly 50 nucleotides away from the payload; the other on the selection cassette (FIG. 3). In this case, we inserted a SNP into the mouse phosphoglycerate kinase (PGK) promoter that drives the expression of a selective resistance marker gene. With these artificially introduced. SNPs, the gene targeting construct could be viewed as a reference-query probe. Hence the gene targeting vector could be used as a RQPS probe. FIG. 3 illustrates different possible fates of the targeting construct in ES cells (HR, homologous recombination, IR; random integration), and predicted ratios of the two linked SNPs to their endogenous counterparts depending upon the type of integration event(s).

As shown in FIG. 3, identification of homologous recombinants (HR) was accomplished by examining the ratio of these artificial SNPs to their endogenous counterparts by quantitative pyrosequencing. Because PGK is on the X chromosome, and most facilities use male (XY) ES cells, only ES cell clones comprising a single integration (homologous or not) is expected to display an allele ratio of 1:1 for the PGK SNP. Any additional integration will increase the fraction of the vector PGK SNP (2 integration-66%, 3-75%, etc.). On the other hand, the HA SNP will only show a 1:1 ratio in homologous recombinants or in cells that underwent 2 random integrations; under all other conditions the fraction of HA SNP will fall either around 33% (one random integration) or above 60% (at least 3 integrations). Therefore, only HR will display a 1:1 ratio for both SNPs.

As a proof of principle, we screened ES cell clones that were transformed by electroporation with one of four different gene targeting constructs. Three of the four vectors were constructed in C57/B6 BAC clones using the BAC recombineering method (Warming, S., et al., Nucleic Acids Res. 33: e36, 2005), during which process the desired SNPs were incorporated (FIG. 4). Although our pyrosequencing method is insensitive to the homology arm's length and should work equally well with BAC targeting vectors, we subcloned each targeting construct into plasmids before electroporation into ES cells to facilitate parallel analysis with traditional PCR and Southern blot methods. Of the targeting vectors, two contained only the HA SNP while the other two also contained PGK SNPs. As quantitative pyrosequencing has an error rate within 5%, we collected all clones with pyrosequencing readout between 40% and 60% (50%±2×5%) and tested if we enriched for HR candidates. Our data showed that when only a single SNP was used, a three-fold enrichment was achieved as determined by PCR analysis (FIG. 5, FIG. 7).

Figure 5:
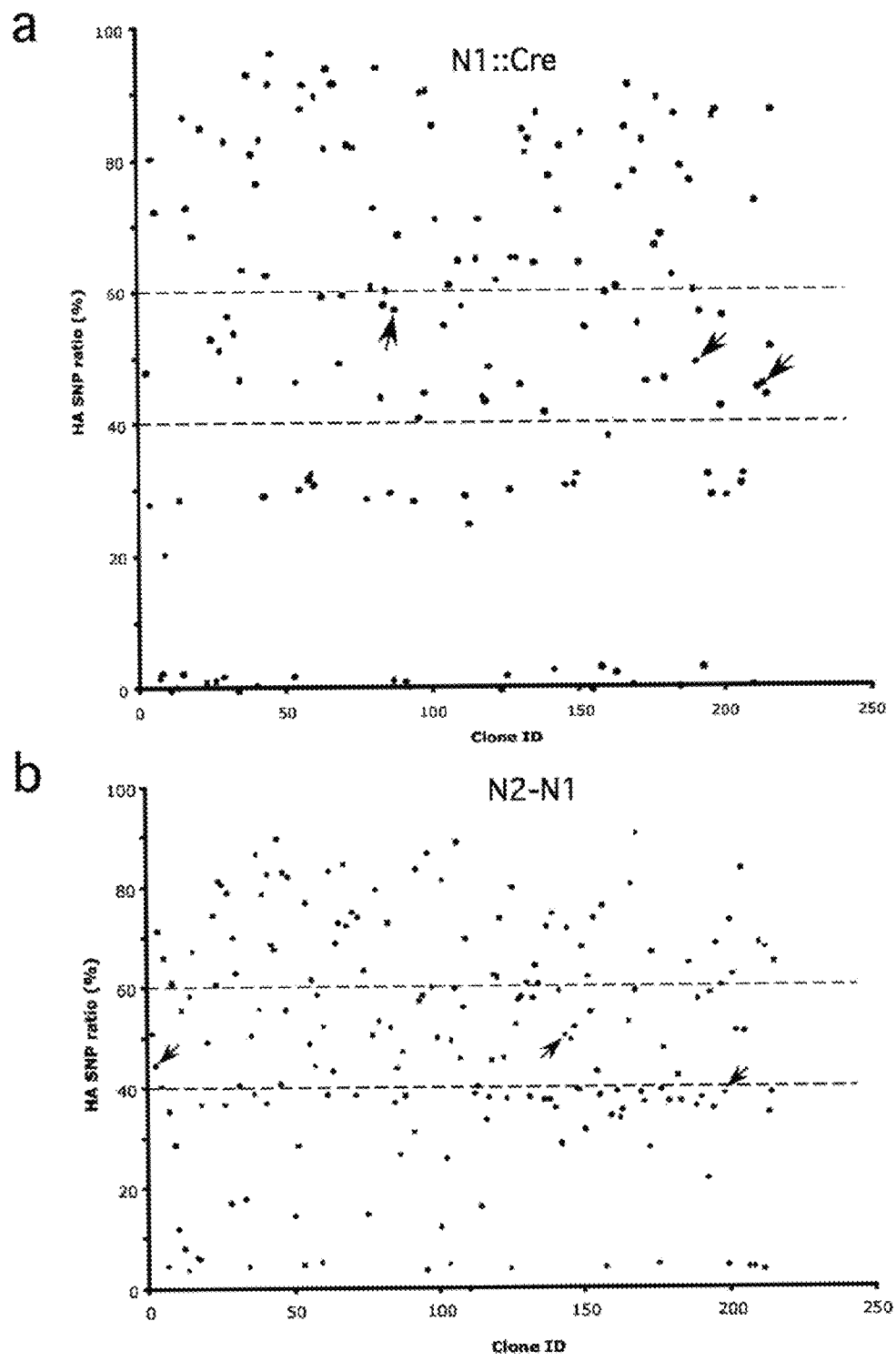
FIG. 5 illustrates screening of ES cells electroporated with N1-Cre (a) and N2-N1 (b) targeting constructs, respectively using the disclosed methods.

In FIG. 5, examples of positive clones identified by PCR and Southern blot are indicated with arrows. FIG. 5a: ES cells electroporated with N1-Cre targeting construct. FIG. 5b: ES cells electroporated with N2-N1 targeting construct. All three N1-cre positive clones fall within the 40-60% SNP readout window while one of three N2-N1 positive clones falls near the window (~38.9).

Figure 6:
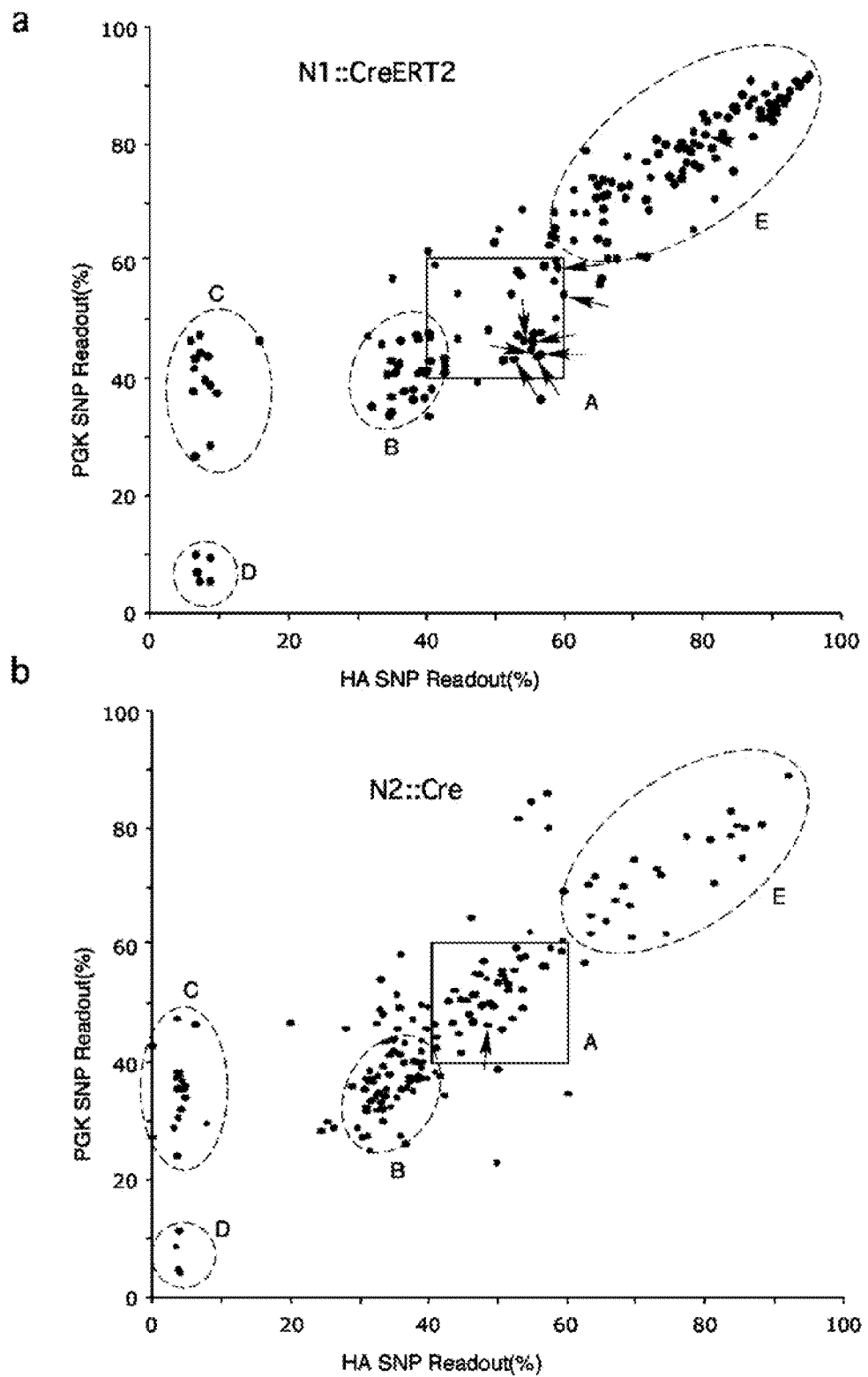
FIG. 6 illustrates screening of ES cells electroporated with either N1-CreERT2 (a) or N2-cre (b) using the disclosed methods.
Figure 7:
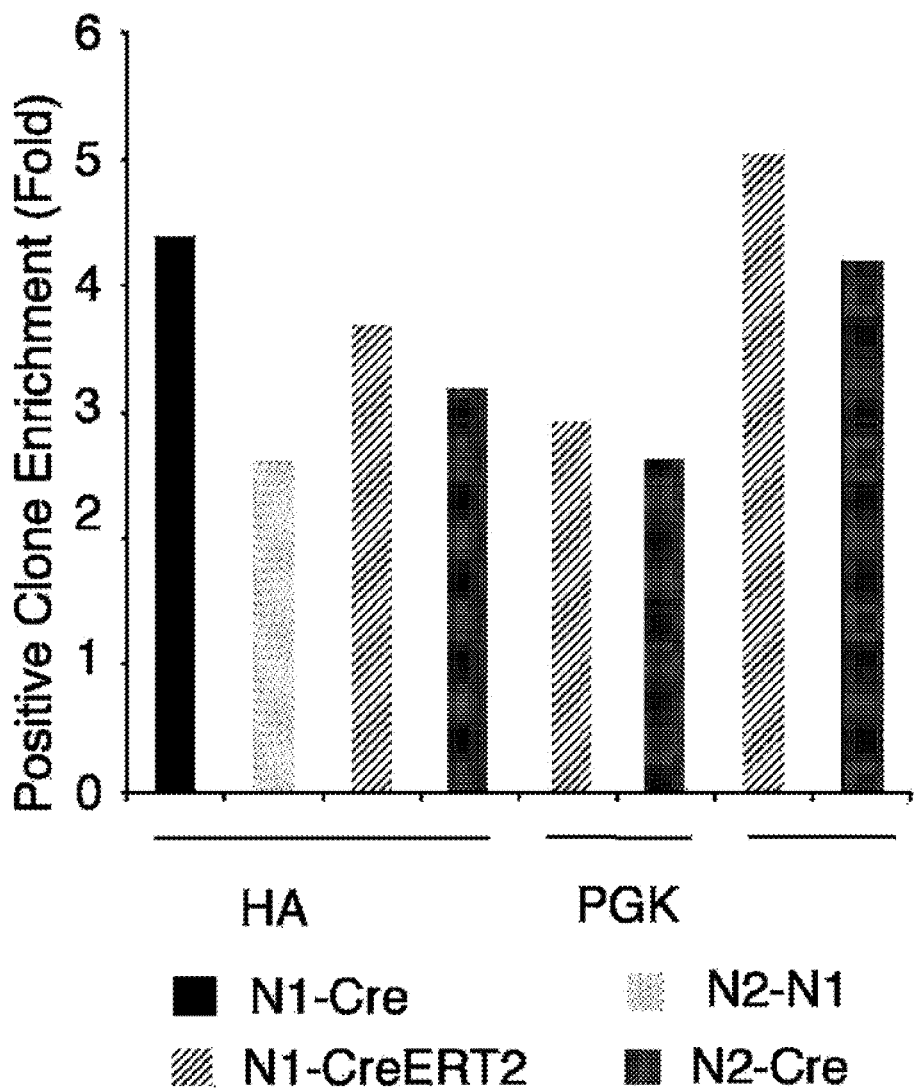
FIG. 7 This figure summarizes results of screening targeted ES cells using the disclosed methods.

With two SNPs, clones with ~50% pyrosequencing readout for both SNPs were examined, attaining a four fold enrichment for HR (FIG. 6, FIG. 7).

In these experiments, ES cells cluster into different groups, as shown in FIG. 6. Group A, both HA and PGK SNP ratio fall between 40-60% (possible HR candidates); group B, HA SNP ratio ~33% and PGK ~40% indicating one randomly integrated copy; group C, indicates only retained one copy of the neomycin selection gene; group D, poorly growing ES cells with heavy MEF contamination. Group E, ES cells that have multiple integrations. Nine out of ten positive clones from N1-CreERT2 9 and one out of one from N2-Cre fall within group A.

FIG. 7 summarizes results of screening targeted ES cells using the disclosed methods. These results show that when only one SNP was employed, the enrichment for positive clones was roughly 3 fold. This enrichment increased to 4 fold when two SNPs were used.

A comparison with traditional PCR and Southern blot screening of the entire population led us to conclude that only 2 of 17 positive HR were not identified by the present methods. We conclude that present methods provide an effective enrichment protocol, and can be used, for example, to streamline an analysis process by eliminating at least 80% of all Neo resistant clones prior to PCR or Southern blot analysis, with an error rate of no greater than ~12% (Table 4).

Example 6

This example illustrates using the present methods to identify ES cells that had undergone homologous recombination by identifying cells that had lost the targeted allele.

In these experiments, we tested 32 ES cell clones to identify cells having a homology arm (HA) SNP and PGK SNP at molar ratios between 40-60%. In these experiments (Table 4), we used the present methods, with a fragment of Notch2 comprising an artificial SNP as a probe reference sequence and the intracellular domain (ICD) of Notch1 comprising an artificial SNP as a probe query sequence.

Figure 8:
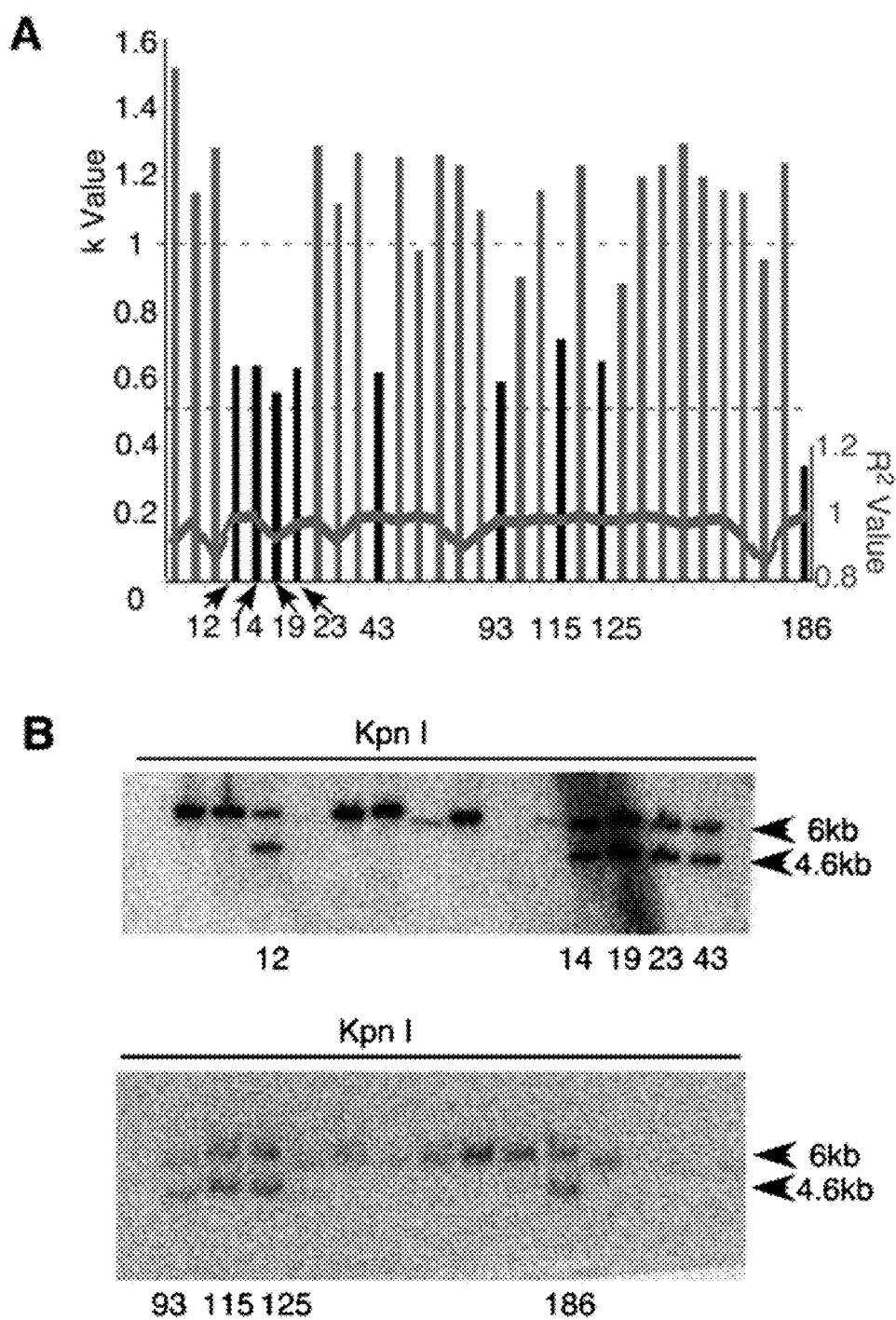
FIG. 8 illustrates further screening of HR clones in targeted ES cells by determining the loss of one copy of the target region using RQPS.

As illustrated in FIG. 8, we identified clones with k values ~1 in addition to 9 clones each with k values near 0.5, consistent with loss of one Notch1 allele. FIG. 8a presents refined screening of 32 ES cells falling within group A (FIG. 6). In these experiments, two different dilutions of an RQPS probe were made with each ES cell genomic DNA sample and pyrosequenced. Black bar represents possible HR clones (clone ID shown) with k values indicating loss of one Notch1 allele. R2 values for zero intercept line are also plotted.

The identity of the 9 clones as homologous recombinants was confirmed by Southern blot. FIG. 8b shows confirmation by Southern blot of a Kpn 1 digestion of genomic DNAs that all HR candidates identified in FIG. 8a contain the WT allele (6 kb) and the targeted allele (4.6 kb).

These results demonstrate that the present methods can be used for pre-screening stem cell lines to identify clones that potentially have insertions as a result of homologous recombination.

Example 7

This example illustrates determining gene copy number in human patients using RPQS.

The present inventors tested whether RQPS could be used to measure gene copy number in seven human patient samples previously found to have duplication or loss of specific loci with array-CGH. Without knowing if loss of homozygosity (LOH) or duplication had occurred, the samples were subjected, in a semi-blind manner, to RQPS using probes consisting of small DNA fragments from genes located in the aberrant region, as query, and NOTCH2, as reference. The results obtained from five samples by RQPS were consistent with array-CGH data, including all four LOH cases and one duplication (Table 1). However, RQPS results conflicted with array-CGH for two samples. In both cases, the readout from RQPS was smaller (two copies by RQPS vs. three copies by array-CGH). Since the RQPS probes did not overlap with array-CGH probes, this could reflect a scenario wherein the region covered by the 60-bp-long array probe is duplicated, whereas the region detected by our RQPS probe is not. Indeed, when RQPS probes were redesigned to match the array-CGH probes, the two methods produced consistent results, identifying duplication in both loci. The discrepancy between the exact copy numbers (three copies vs. four copies) may not be surprising since probe response to ratio change in oligonucleotide arrays tends to be suppressed (Carter, N. P., Nat. Genet. 39: S16-S21, 2007).

These data demonstrate that RQPS offers an alternative for confirmation of array-CGH results and is particularly effective in detecting defined deletions/amplifications. RQPS can be also used to map the boundaries of copy number variations.

All references, publications, patents and patent applications cited herein are incorporated by reference, each in its entirety.

TABLE 1

CNV analysis in human patient samples by RQPS. For each sample, an RQPS probe, consisting of an exon fragment (~50 bp) from within a randomly selected query gene residing within the CNV region fused to a Notch2 fragment, was prepared. Both fragments were mutated to contain an SNV. These probes were then used to estimate the copy number of seven loci in a semi blind test. After RQPS, the results were compared to previously determined array-CGH data. Two discrepancies were found, which were resolved when RQPS was repeated with query sequences matching the CGH probe.

| Patient | Region | Genes | RQPS probe (Query) | Estimated Copy Number by RQPS | Estimated Copy Number by Array-CGH |
|---|---|---|---|---|---|
| 1 | Chr. 12: 51493655-52217545 | MAP3K12; SP1; KRT18; ZNF740 | SP1 exon3 | $2^2$ | 3 |
| $1^1$ | Chr. 12: 51493655-52217545 | MAP3K12; SP1; KRT18; ZNF740 | SP1 CGH probe region | $4^3$ | 3 |
| 2 | Chr. 22: 46857948-tel | TRABD; MAPK12; FAM19A5 | TRABD | 1 | 1 |
| 3 | Chr. 2: 88110094-88925173 | SMYD1; FABP1; RPIA; EIF2AK3 | FABP1 exon1 | $2^2$ | 3 |
| $3^1$ | Chr. 2: 88110094-88925173 | SMYD1; FABP1; RPIA; EIF2AK3 | FABP1 CGH probe region | $4^3$ | 3 |
| 4 | Chr. 9: 2924366-4409742 | RFX3; GLIS3 | RFX3 | 1 | 1 |
| 5 | Chr. 9: tel-24136507/Chr.13: 19558594-36717548 | RFX3; GLIS3; JAK2; PSIP1; MTAP; BRCA2; SMAD9; SACS; TNFRSF19 | SMAD9 | 3 | 3 |
| 6 | Chr. 17: 7122558-7868524 | TP53; TNK1; NLGN2; ATP1B2; FGF11; SOX15 | FGF11 | 1 | 1 |
| 7 | Chr. 18: 957962-12021803 | RAB12; ARHGAP28; RALBP1; NAPG | RALBP1 | 1 | 1 |

[1] Repeat reaction with RQPS probe matching the CGH probe.
[2] Inconsistent result between RQPS probe to a region not covered by a CGH probe and the CGH array.
[3] Both RQPS and array-CGH data detected amplification; they differ in estimating copy number.

TABLE 2

Primers and expected size of PCR product used for the screening of ES cells

| Targeting constructs | Upstream Outer Primer | Upstream Inner Primer |
|---|---|---|
| N1Cre | AACCAAACACCAGGCTCCTG (SEQ ID NO: 1) | ATCCCTGCCCATTGCGAGTC (SEQ ID NO: 2) |
| N2-N1 | CGGTGTTGGGTCGTTTGTTC (SEQ ID NO: 3) | TCGATACCCCACCGAGACC (SEQ ID NO: 4) |
| N1creERT2 | CGGTGTTGGGTCGTTTGTTC (SEQ ID NO: 5) | TCGATACCCCACCGAGACC (SEQ ID NO: 6) |
| N2-cre | AGACAGGGTTTCTCTTTGTAGC (SEQ ID NO: 7) | CTGTCCTGGAACTCACTCTGTAG (SEQ ID NO: 8) |

| Targeting constructs | Downstream Inner Primer | Downstream Outer Primer |
|---|---|---|
| N1Cre | CGTTGCATCGACCGGTAATG (SEQ ID NO: 9) | ACATGTCCATCAGGTTCTTG (SEQ ID NO: 10) |
| N2-N1 | CAGCTAAGGAAACCCAGCAG (SEQ ID NO: 11) | GGACTGTCTCCAGGTTGTGC (SEQ ID NO: 12) |
| N1creERT2 | CACAGCCACCAGGGACAGAA (SEQ ID NO: 13) | TTGCAGGCCTTAAGAGACAG (SEQ ID NO: 14) |
| N2-cre | CGTTGCATCGACCGGTAATG (SEQ ID NO: 15) | ACATGTCCATCAGGTTCTTG (SEQ ID NO: 16) |

TABLE 2-continued

Primers and expected size of PCR product used for the screening of ES cells

| Targeting constructs | Expected PCR Product Size |
|---|---|
| N1Cre | 2.8 kb |
| N2-N1 | 4.8 kb |
| N1creERT2 | 2.6 kb |
| N2-cre | 4.7 k b |

TABLE 3

Primers for pyrosequencing reaction

| | SNP | Untailed Primer |
|---|---|---|
| Notch1 HA | agctgcacctC/Atgtacgtgg (SEQ ID NO: 17, SEQ ID NO: 18) | ACAGCCCACAAAGAACAGGAGC (SEQ ID NO: 19) |
| Notch2 HA | tcatcatcctG/Cttcttcatcc (SEQ ID NO: 20, SEQ ID NO: 21) | ATGATGACCCCCAGCAGGA (SEQ ID NO: 22) |
| mPGK | acacattccaC/Gatccaccggt (SEQ ID NO: 23, SEQ ID NO: 24) | CTCTGGCCTCGCACACATTQ (SEQ ID NO: 25) |
| Notch1 ICD | gtttcaaagtG/Ctcagaggcca (SEQ ID NO: 26, SEQ ID NO: 27) | ATGGCCAGCTCTGGTTCC (SEQ ID NO: 28) |
| Cre | aaaatgcttcT/Cgtccgtttgc (SEQ ID NO: 29, SEQ ID NO: 30) | GAGTGATGAGGTTCGCAAGAA (SEQ ID NO: 31) |
| V to G | ggctgtggggT/Ggctgctgtcc (SEQ ID NO: 32, SEQ ID NO: 33) | TCCTGTTCTTTGTGGGCTGTG (SEQ ID NO: 34) |

| | Tailed Primer* | Sequencing Primer |
|---|---|---|
| Notch1 HA | CAGCATCACCACGCCTGAC (SEQ ID NO: 35) | CGCTGCCACGTACAT (SEQ ID NO: 36) |
| Notch2 HA | TATCTGCTCGCGGTCGCT (SEQ ID NO: 37) | CCCCAGCAGGATGAA (SEQ ID NO: 38) |
| mPGK | GGGCCACCAAAGAACGGA (SEQ ID NO: 39) | GGCCTCGCACACATT (SEQ ID NO: 40) |
| Notch1 ICD | GGGCTCTCTCCGCTTCTTCT (SEQ ID NO: 41) | TCCCTGAGGGTTTCAA (SEQ ID NO: 42) |
| Cre | CCGGTTATTCAACTTGCACCAT (SEQ ID NO: 43) | CATACCTGGAAAATGCTT (SEQ ID ID NO: 44) |
| V to G | CTGGCCTCTGACACTTTGAAACC (SEQ ID NO: 45) | TTGTGGGCTGTGGGG (SEQ ID NO: 46) |

*A common tail (5'-AGCGCTGCTCCGGTTCATAGATT-3', (SEQ ID NO: 47)) is added to the 5' end of each tailed primer

TABLE 4

Statistical Data on the pryoscreening of ES cells electroporated with four different targeting constructs

| Constructs | # of ES cells screened | SNP used for pyroscreening | # of ES cells with pyrosequcing readout between 40-60% | # of positive clones falling within 40-60% window | # of positive clones falling out of 40-60% window | Fold of positive clone enrichment |
|---|---|---|---|---|---|---|
| N1-cre | 150 | HA | 34 | 3 | 0 | 4.4 |
| N2-N1 | 181 | HA | 48 | 2 | 1 | 2.5 |
| | | HA | 46 | | | 3.5 |
| N1-CreERT2 | 178 | PGK | 57 | 9 | 1 | 2.8 |
| | | HA + PGK | 32 | | | 5.0 |
| | | HA | 55 | | | 3.2 |

TABLE 4-continued

Statistical Data on the pryoscreening of ES cells electroporated with four different targeting constructs

| Constructs | # of ES cells screened | SNP used for pyroscreening | # of ES cells with pyrosequcing readout between 40-60% | # of positive clones falling within 40-60% window | # of positive clones falling out of 40-60% window | Fold of positive clone enrichment |
|---|---|---|---|---|---|---|
| N2-cre | 174 | PGK | 68 | 1 | 0 | 2.6 |
|  |  | HA + PGK | 41 |  |  | 4.2 |

What is claimed is:

1. A method of determining in a sample, the molar ratio of a query locus to a reference locus, the method comprising:
   1) forming one or more mixtures, each mixture comprising: a) a reference-query coupled probe comprising a nucleobase polymer comprising i) a probe reference locus comprising a probe reference allele, and ii) a probe query locus comprising a probe query allele, and b) a sample comprising i) a sample reference locus comprising a sample reference allele and ii) a sample query locus comprising 0 or greater copies of a sample query allele;
   2) determining for each mixture a) the amount of probe reference allele as a fraction of total reference allele and b) the amount of probe query allele as a fraction of total query allele; and
   3) calculating the molar ratio of the sample query allele to the sample reference allele.

2. A method in accordance with claim 1, wherein the one or more mixtures comprises at least 2 mixtures, wherein the molar ratio of the sample reference locus to the probe reference locus of at least one first mixture does not equal the molar ratio of the sample reference locus to the probe reference locus of at least one second mixture.

3. A method in accordance with claim 1, wherein the nucleobase polymer is a nucleic acid.

4. A method in accordance with claim 3, wherein the nucleic acid is selected from the group consisting of a single-stranded DNA, a double-stranded DNA, a single-stranded RNA and a double-stranded RNA.

5. A method in accordance with claim 1, wherein the sample reference allele comprises a sample reference SNP allele, the sample query allele comprises a sample query SNP allele, the probe reference allele comprises a probe reference SNP allele, and the probe query allele comprises a probe query SNP allele.

6. A method in accordance with claim 5, wherein the determining the molar ratios comprises sequencing each locus by pyrosequencing.

7. A method in accordance with claim 1, wherein for each mixture the molar ratio of the probe reference allele to the sample reference allele is from about 1:9 to about 9:1.

8. A method in accordance with claim 1, wherein the sample query locus comprising a 0 or greater copies of a sample query allele is a sample query locus comprising 1 or greater copies of the sample query allele.

9. A method in accordance with claim 1, wherein the sample comprises DNA of an animal.

10. A method in accordance with claim 9, wherein the animal is a mammal.

11. A method in accordance with claim 10, wherein the mammal is selected from the group consisting of a rodent, a farm animal, a companion animal, and a human.

12. A method in accordance with claim 1, wherein the sample reference locus is a haploinsufficient locus.

13. A method in accordance with claim 1, wherein the sample comprises genomic DNA of a transformed or transfected stem cell.

14. A reference-query coupled probe, comprising a nucleobase polymer comprising a) a reference locus comprising a probe reference allele, and b) a probe query locus comprising a probe query allele.

15. A reference-query coupled probe of claim 14, wherein the probe reference allele comprises a probe reference SNP.

16. A reference-query coupled probe of claim 14, wherein the probe query allele comprises a probe query SNP.

17. A reference-query coupled probe of claim 14, wherein the probe reference allele comprises a probe reference SNP and the probe query allele comprises a probe query SNP.

18. A mixture comprising a sample and the reference-query probe of claim 14.

* * * * *

SEQUENCE LISTING

<160> NUMBER OF SEQ ID NOS: 47

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aaccaaacac caggctcctg                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
atccctgccc attgcgagtc                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cggtgttggg tcgtttgttc                                              20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
tcgatacccc accgagacc                                               19

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cggtgttggg tcgtttgttc                                              20

```
<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
tcgatacccc accgagacc                                                   19

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
agacagggtt tctctttgta gc                                               22

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
ctgtcctgga actcactctg tag                                              23

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cgttgcatcg accggtaatg                                                  20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
acatgtccat caggttcttg                                                  20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cagctaagga aacccagcag                                                  20

<210> SEQ ID NO 12
<211> LENGTH: 20
<212> TYPE: DNA
<213> ORGANISM: Artificial Sequence
<220> FEATURE:
<223> OTHER INFORMATION: primer
```

-continued

```
<400> SEQUENCE: 12
ggactgtctc caggttgtgc                                                   20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cacagccacc agggacagaa                                                   20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ttgcaggcct taagagacag                                                   20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cgttgcatcg accggtaatg                                                   20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
acatgtccat caggttcttg                                                   20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
agctgcacct ctgtacgtgg                                                   20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
agctgcacct atgtacgtgg                                                   20

<210> SEQ ID NO 19
<211> LENGTH: 22
<212> TYPE: DNA
```

```
<213> ORGANISM: Artificial Sequence
<220> FEATURE:
<223> OTHER INFORMATION: primer

<400> SEQUENCE: 19
acagcccaca aagaacagga gc                                              22

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
tcatcatcct gttcttcatc c                                               21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
tcatcatcct cttcttcatc c                                               21

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
atgatgaccc ccagcagga                                                  19

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
acacattcca catccaccgg t                                               21

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
acacattcca gatccaccgg t                                               21

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
ctctggcctc gcacacatt                                                  19
```

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gtttcaaagt gtcagaggcc a                                              21

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
gtttcaaagt ctcagaggcc a                                              21

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
atggccagct ctggttcc                                                  18

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
aaaatgcttc tgtccgtttg c                                              21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
aaaatgcttc cgtccgtttg c                                              21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gagtgatgag gttcgcaaga a                                              21

<210> SEQ ID NO 32
<211> LENGTH: 21
<212> TYPE: DNA
<213> ORGANISM: Artificial Sequence
<220> FEATURE:
<223> OTHER INFORMATION: primer -continued

<400> SEQUENCE: 32
ggctgtgggg tgctgctgtc c                                              21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
ggctgtgggg ggctgctgtc c                                              21

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
tcctgttctt tgtgggctgt g                                              21

<210> SEQ ID NO 35
<211> LENGTH: 19
<212> TYPE: DNA
<213> ORGANISM: Artificial Sequence
<220> FEATURE:
<223> OTHER INFORMATION: primer

<400> SEQUENCE: 35
cagcatcacc acgcctgac                                                 19

<210> SEQ ID NO 36
<211> LENGTH: 15
<212> TYPE: DNA
<213> ORGANISM: Artificial Sequence
<220> FEATURE:
<223> OTHER INFORMATION: primer

<400> SEQUENCE: 36
cgctgccacg tacat                                                     15

<210> SEQ ID NO 37
<211> LENGTH: 18
<212> TYPE: DNA
<213> ORGANISM: Artificial Sequence
<220> FEATURE:
<223> OTHER INFORMATION: primer

<400> SEQUENCE: 37
tatctgctcg cggtcgct                                                  18

<210> SEQ ID NO 38
<211> LENGTH: 15
<212> TYPE: DNA
<213> ORGANISM: Artificial Sequence
<220> FEATURE:
<223> OTHER INFORMATION: primer

<400> SEQUENCE: 38
ccccagcagg atgaa                                                     15

<210> SEQ ID NO 39
<211> LENGTH: 18
<212> TYPE: DNA

<213> ORGANISM: Artificial Sequence
<220> FEATURE:
<223> OTHER INFORMATION: primer

<400> SEQUENCE: 39
gggccaccaa agaacgga                                                18

<210> SEQ ID NO 40
<211> LENGTH: 15
<212> TYPE: DNA
<213> ORGANISM: Artificial Sequence
<220> FEATURE:
<223> OTHER INFORMATION: primer

<400> SEQUENCE: 40
ggcctcgcac acatt                                                   15

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gggctctctc cgcttcttct                                              20

<210> SEQ ID NO 42
<211> LENGTH: 16
<212> TYPE: DNA
<213> ORGANISM: Artificial Sequence
<220> FEATURE:
<223> OTHER INFORMATION: primer

<400> SEQUENCE: 42
tccctgaggg tttcaa                                                  16

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
ccggttattc aacttgcacc at                                           22

<210> SEQ ID NO 44
<211> LENGTH: 18
<212> TYPE: DNA
<213> ORGANISM: Artificial Sequence
<220> FEATURE:
<223> OTHER INFORMATION: primer

<400> SEQUENCE: 44
catacctgga aaatgctt                                                18

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
ctggcctctg acactttgaa acc                                          23

```
<210> SEQ ID NO 46
<211> LENGTH: 15
<212> TYPE: DNA
<213> ORGANISM: Artificial Sequence
<220> FEATURE:
<223> OTHER INFORMATION: primer

<400> SEQUENCE: 46
ttgtgggctg tgggg                                                      15

<210> SEQ ID NO 47
<211> LENGTH: 23
<212> TYPE: DNA
<213> ORGANISM: Artificial Sequence
<220> FEATURE:
<223> OTHER INFORMATION: primer

<400> SEQUENCE: 47
agcgctgctc cggttcatag att                                             23
```